United States Patent
Bruce et al.

(10) Patent No.: US 10,730,960 B2
(45) Date of Patent: *Aug. 4, 2020

(54) DEXTRAN SULFATE

(71) Applicant: TX Medic AB, Viken (SE)

(72) Inventors: Lars Bruce, Viken (SE); Ulf Brasen, Quarteira (PT)

(73) Assignee: TX MEDIC AB, Viken (SE)

(*) Notice: Subject to any disclaimer, the term of this patent is extended or adjusted under 35 U.S.C. 154(b) by 0 days.

This patent is subject to a terminal disclaimer.

(21) Appl. No.: 16/520,930

(22) Filed: Jul. 24, 2019

(65) Prior Publication Data

US 2019/0375859 A1 Dec. 12, 2019

Related U.S. Application Data

(63) Continuation of application No. 15/525,818, filed as application No. PCT/SE2015/051188 on Nov. 10, 2015, now Pat. No. 10,407,514.

(30) Foreign Application Priority Data

Nov. 11, 2014 (SE) ...................................... 1451349

(51) Int. Cl.
C08B 37/02 (2006.01)
A61P 29/00 (2006.01)
C08L 5/02 (2006.01)

(52) U.S. Cl.
CPC ............ *C08B 37/0021* (2013.01); *C08L 5/02* (2013.01); *A61P 29/00* (2018.01); *C08L 2203/02* (2013.01)

(58) Field of Classification Search
CPC .............................. C08B 37/0021; A61P 29/00
See application file for complete search history.

(56) References Cited

U.S. PATENT DOCUMENTS

| | | | |
|---|---|---|---|
| 3,141,014 A | 7/1964 | Eji Morii et al. | |
| 4,221,907 A | 9/1980 | Nair et al. | |
| 4,232,150 A | 11/1980 | Nair et al. | |
| 4,840,941 A | 6/1989 | Ueno et al. | |
| 4,855,416 A | 8/1989 | Usher | |
| 5,736,506 A | 4/1998 | Naka | |
| 5,849,689 A | 12/1998 | Chamow et al. | |
| 6,143,730 A | 11/2000 | Parish et al. | |
| 8,629,123 B2 | 1/2014 | Nilsson et al. | |
| 8,901,104 B2 | 12/2014 | Nilsson et al. | |
| 8,906,884 B2 | 12/2014 | Nilsson et al. | |
| 9,364,499 B2 | 6/2016 | Nilsson et al. | |
| 10,307,440 B2 | 6/2019 | Nilsson et al. | |
| 2004/0009953 A1 | 1/2004 | Comper | |
| 2004/0242801 A1 | 12/2004 | Petit et al. | |
| 2010/0113389 A1* | 5/2010 | Nilsson ................ A61K 31/721 514/59 |
| 2011/0008343 A1 | 1/2011 | Lambris et al. | |
| 2016/0120897 A1 | 5/2016 | Waas et al. | |

FOREIGN PATENT DOCUMENTS

| | | |
|---|---|---|
| CN | 1347919 A | 5/2002 |
| CN | 103554297 A | 2/2014 |
| EP | 0251134 A2 | 1/1988 |
| EP | 0375976 A3 | 9/1991 |
| JP | 46-9570 | 3/1971 |
| JP | 47-30167 | 8/1972 |
| JP | 02262521 A | 10/1990 |
| JP | 8-301771 A | 11/1996 |
| JP | 2000-178196 A | 6/2000 |
| JP | 2016-519143 A5 | 6/2017 |
| WO | 2004/047848 A1 | 6/2004 |

OTHER PUBLICATIONS

Definition of prevent, Oxford English Dictionary Online, http://dictionary.oed.com/, accessed online Mar. 27, 2010, especially definition 9a. at p. 2. (Year: 2010).*
Wiley, J., Xenotransplantation, 2008, 15(4), p. 225-234, Author Manuscript, 18pgs. (Year: 2008).*
Hosoya et al., Differential Inhibitory Effects of Sulfated Polysaccharides and Polymers on the Replication of Various Myxoviruses and Retroviruses, Depending on the Composition of the Target Amino Acid Sequences of the Viral Envelope Glycoproteins, Antimicrobial Agents and Chemotherapy, vol. 35, No. 12, p. 2515-2520 (Dec. 1991).
Ricketts et al., Blood Anticoagulants, With Special Reference to Dextran Sulphate, Chemistry and Industry, p. 869-871 (Sep. 6, 1952).
Kunou, M. et al., The effect of growth factors on the cytotoxicity of sulphated polysaccharides, Carbohydrate Polymers, vol. 34, No. 4, pp. 335-342 (1997).
Novikova, E.V. et al., Sulfation of dextran with Chlorosulfonic acid in organic solvents, Russian Journal of Applied Chemistry, vol. 80, No. 7, pp. 1151-1153 (2007).
Mihai, D. et al., Chemical reactions on polysaccharides 1. Pullulan sulfation, European Polymer Journal, vol. 37, pp. 541-546 (2001).
Hartzell G. Payne et al., Sulfated dextran—blood anticoagulant activity and toxicity studies in animals, The American Journal of Medical Technology, vol. 19, No. 5, pp. 219-227 (1953).
Neville, G. A. et al., Characterization and differentiation of some complex dextran sulfate preparations of medicinal interest, Journal of Pharmaceutical Sciences, vol. 80, No. 3, pp. 239-244 (1991).
Papy-Garcia, D. et al., Nondegradative sulfation of polysaccharides. Synthesis and structure characterization of biologically active heparan sulfate mimetics, Macromolecules, vol. 38, No. 11, pp. 4647-4654 (2005).

(Continued)

Primary Examiner — Jonathan S Lau
(74) Attorney, Agent, or Firm — Porter Wright Morris & Arthur LLP

(57) ABSTRACT

Methods of treating, inhibiting and/or preventing instant blood-mediated inflammatory reaction (IBMIR) comprise administering, to a subject, a dextran sulfate characterized by a number average molecular weight ($M_n$) as measured by nuclear magnetic resonance (NMR) spectroscopy within an interval of 1850 and 3500 Da; an average sulfate number per glucose unit within an interval of 2.5 and 3.0; and an average sulfation of C2 position in the glucose units of said dextran sulfate of at least 90%, or a salt of such a dextran sulfate.

22 Claims, 14 Drawing Sheets

(56) References Cited

OTHER PUBLICATIONS

Mahner, C. et al., Synthesis and characterisation of dextran and pullulan sulphate, Carbohydrate Research, vol. 331, pp. 203-208 (2001).
Sasaki, S. et al., Toxicity of heparinoids with special reference to the precipitation of fibrinogen, Thrombosis et Diathesis Haemorrhagica, vol. 12, No. 1-2, pp. 232-261 (1964).
Ricketts, C.R., Dextran Sulphate—A Synthetic Analogue of Heparin, Biochem, vol. 51, pp. 129-133 (1952).
Hatanaka et al., J. Med Chem., 1987, 30, pp. 810-814 (1987).
Fiorante, P. et al, "Low molecular weight dextran sulfate prevents complement activation and delays hyperacute rejection in pig-to-human xenotransplantation models". Xenotransplantation, 8(I):24-35 (2001).
Baldwin, William M. et al, "Complement in Organ Transplantation", Transplantation, vol. 59, No. 6, pp. 797-808 (1995).
Bennet, W. et al, "Damage to porcine islets of Langerhans after exposure to human blood in vitro, or after intraportal transplantation to cynomologus monkeys: protective effects of sCRI and heparin", Transplantation, vol. 69, No. 2, pp. 711-719 (2000)—abstract.
Nakano, M. et al, "Hepatocyte growth factor is essential for amelioration of hyperglycemia in streptozotocin-induced diabetic mice receiving a marginal mass of intrahepatic islet grafts". Transplantation, vol. 69, No. 2, pp. 214-221 (2000).
Thomas, Helen et al, "Sulfonated dextran inhibits complement activation and complement-dependent cytotoxicity in an in vitro model of hyperacute xenograft rejection", Mol. Immunol., vol. 33, No. 7-8, pp. 643-648 (1996)—abstract.
Shapiro, A.M. James et al, "Islet Transplantation in Seven Patients with Type I Diabetes Mellitus Using a Glucocorticoid-Free Immunosuppressive Regimen", N. Engl J. Med., vol. 343, No. 4, pp. 230-238 (2000)—abstract.
Pratt, J.R. et al, "Effects of complement inhibition with soluble complement receptor-1 on vascular injury and inflammation during renal allograft rejection in the rat". Am J. Pathol., vol. 149, No. 6, pp. 2055-2066 (1996).
Carroll, Michael C. et al, "Complement and the immune response", Curr. Opin. Immunol., 9(I):64-69 (1997)—abstract.
Catarovich, Diego et al, "Rapid failure of pig islet transplantation in non human primates". Xenotransplantation, 9 (I):25-35 (2002)—abstract.
Buhler, L. et al, "Adult porcine islet transplantation in baboons treated with conventional immunosuppression or a non-myeloablative regimen and CD 154 blockade". Xenotransplantation, 9(1):3-13 (2002)—abstract.
Bennet, William et al, "Incompatibility Between Human Blood and Isolated Islets of Langerhans", Diabetes, vol. 48, Oct. 1999, pp. 1907-1914.
Ryan, Edmond A. et al, "Clinical Outcomes and Insulin Secretion After Islet Transplantation With the Edmonton Protocol", Diabetes, vol. 50, Apr. 2001, pp. 710-719.
Wuillemin, Walter A. et al, "Potentiation of CI Inhibitor by Glycosaminoglycans", The Journal of Immunology, 1997, pp. 1953-1960.
Babock et al, Immunology, 33(6):925-929 (1977)—Abstract.
Zioncheck et al, "Sulfated Oligosaccharides Promote Hepatocyte Growth Factor Association and Govern its Mitogenic Activity", Journal of Biological Chemistry, 270(28)16871-78 (1995).
Kaibori et al, "Stimulation of liver regeneration and function after partial hepatectomy in cirrhotic rats by continuous infusion of recombinant human hepatocyte growth factor", Journal of Heptatology, 27:381-390 (1997).
Richardson et al, Journal of Bacteriology, 1968, 96(4): 1443-1445.

McCoy, David G. et al., Characterization of Dextran Sulfate-treated Ascites Tumor Cells and Their Repair by Ascites Fluid, Cancer Res, vol. 36, pp. 3339-3345 (1976).
Clarke, G. D. et al., Conditions Affecting the Response of Cultured Cells to Serum, Growth Control in Cell Cultures, pp. 17-28 (1971).
Goto, M. et al., Decrease of Saturation Density of Cells of Hamster Cell Lines after Treatment with Dextran Sulfate, Experimental Cell Research, vol. 82, pp. 367-374 (1973).
Scholnick, Perry et al., Regulatory Mechanisms in Carbohydrate Metabolism, The Journal of Biological Chemistry, vol. 248, No. 14, pp. 5175-5182 (Jul. 25, 1973).
Hiebert, Linda M. et al., Dextran Suphates Protect Procine Arterial Endothelial Cells from Free Radical Injury, Human & Experimental Toxicology, vol. 13, pp. 233-239 (1994).
Eriksson et al "Positron Emission Tomography in Clinical Islet Transplantation", American Journal of Transplantation, 9:2816-2824 (2009).
Eich et al, "Positron Emission Tomography: A Real-Time Tool to Quantify Early Islet Engraftment in a Preclinical Large Animal Model", Transplantation, 84(7):893-898 (2007).
Eich et al, "Visualization of Early Engraftment in Clinical Islet Transplantation by Positron-Emission Tomography", New England Journal of Medicine, 356(26):2754-2755 (2007).
Hall, M. et al., The Use of Dextran Sulphate as a Blood Anticoagulant in Biological Research, J. Clin. Path., vol. 5, pp. 366 (1952).
Holahan, Matthew R. et al., Intra-Accumbens Injection of a Dopamine Aptamer Abates MK-801-Induced Cognitive Dysfunction in a Model of Schizophrenia, PLOS ONE, vol. 6, No. 7, pp. 1-8 (Jul. 2011).
Rood, Pleunie P. M. et al., Reduction of Early Graft Loss After Intraportal Porcine Islet Transplantation in Monkeys, Transplantation, vol. 83, No. 2, pp. 202-210 (Jan. 27, 2007).
Naziruddin, B. et al., Evidence for Instant Blood-Mediated Inflammatory Reaction in Clinical Autologous Islet Transplantation, The American Society of Transmplantation, vol. 14, pp. 428-437 (2014).
Johansson, H. et al., Low Molecular Weight Dextran Sulfate: A Strong Candidate Drug to Block IBMIR in Clinical Islet Transplantation, American Journal of Transplantation, vol. 6, pp. 305-312 (2006).
Goto, Masafumi et al., Low Molecular Weight Dextran Sulfate Prevents the Instant Blood-Mediated Inflammatory Reaction Induced by Adult Porcine Islets, Transplantation, vol. 77, pp. 741-747 (Mar. 15, 2004).
Goto, Masafumi et al., Abstract 067, Low molecular weight dextran sulfate abrogates the instant blood-mediated inflammatory reaction induced by adult porcine islets both in vitro and in vivo, Transplantation, vol. 76, No. 4, pp. S40-S41 (2003).
Wiley, John, Dissecting the instant blood-mediated inflammatory reaction in islet xenotransplantation, Xenotransplantation, vol. 15, No. 4, pp. 225-234 (2008).
Caplus Accession No. 1984:503758 (Abstract of Huang et al, Zhongcaoyao, 15(5):213-216) (1984).
Deboer K. F. et al., Intra-Uterine Device and Embryonic Survival in the Rat, J. Reprod. Fert., vol. 21, pp. 343-346 (1970).
Protocols Online, Tris-Buffered Saline (TBS), pp. 1-3 (Jul. 14, 2012).
Huang et al., (Zhongcaoyao (1984), 15(5), 213-16)—abstract.
Sergeev et al., Effect of Stimulation of Antibody Formation by Bone Marrow Cells in vivo, vol. 85, pp. 447-449 (Apr. 1978).
Zatz, Marion M. et al., The Distribution of 51CR-Labeled Lymphocytes inot Antigen-Stimulated Mice, vol. 134, pp. 224-241 (1971).
Davis, Starkey D. et al., Volumes of Injections in Mice, The Journal of Infectious Diseases, vol. 130, No. 2, pp. 209-211 (Aug. 1974).
Goto, et al., Low-Molecular Weight Dextran Sulfate Abrogates the Instant Blood-Mediated Inflammatory Reaction Induced by Adult Porcine Islets Both in Vitro and In Vivo, Transplantation, vol. 36, pp. 1186-1187 (2004).

* cited by examiner

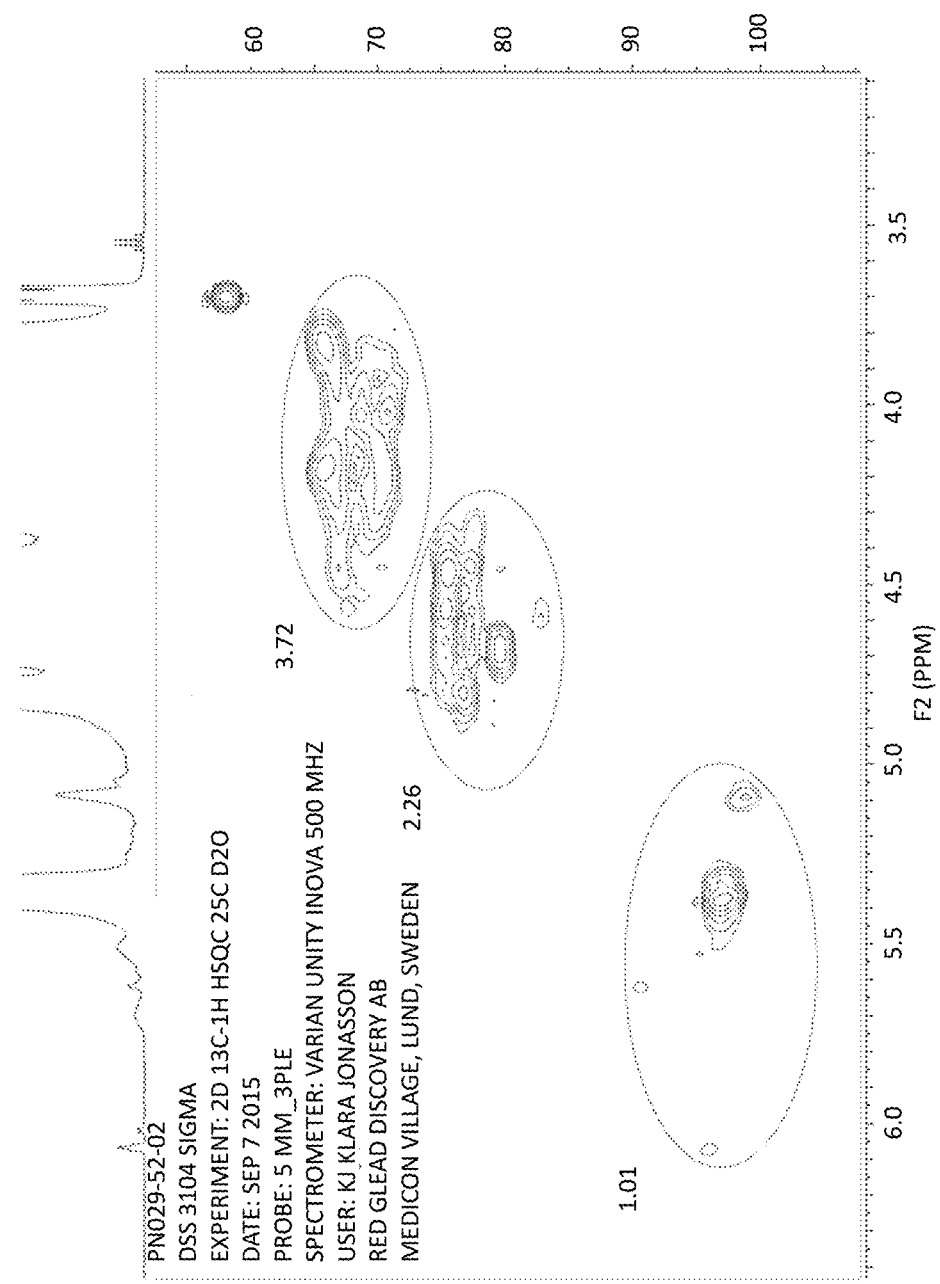

DEXTRAN SULFATE

CROSS-REFERENCE TO RELATED APPLICATIONS

This application is a continuation application of U.S. patent application Ser. No. 15/525,818, filed May 10, 2017, which is a 371 of PCT/SE2015/051188 filed Nov. 10, 2015.

TECHNICAL FIELD

The present embodiments generally relate to dextran sulfate, and in particular to a new dextran sulfate having improved biological effect and low toxicity.

BACKGROUND

Dextran is a complex, branched glucan, i.e. a polysaccharide made of glucose units, composed of chains of varying lengths typically from one or few thousand Dalton (Da) up to several hundred thousand Da.

The straight chain of dextran consists of α-1,6 glycosidic linkages between glucose units, while branches begin, usually, from α-1,3 linkages. Dextran is synthesized from sucrose by certain lactic acid bacteria, such as *Leuconostoc mesenteroides, Streptococcus mutans* and *Lactobacillus brevis*.

Dextran sulfate is a polyanionic derivative of dextran, in which some of the C2-C4 and end group C1 and C6 positions are sulfated. Dextran sulfate has been known for decades and particularly as a potential substitute for heparin in anticoagulant therapy.

Dextran sulfate molecules are available in different molecular weights, different levels of branching and different sulfate contents and sulfation patterns. These physical and chemical differences among dextran sulfate molecules give rise to different biological and toxic effects.

There is a need for a dextran sulfate having improved biological effects while still not being toxic at pharmaceutically relevant dosages.

SUMMARY

It is a general objective to provide a dextran sulfate having improved biological effects while still not being toxic at pharmaceutically relevant dosages.

This and other objectives are met by embodiments as disclosed herein.

An aspect of the embodiments relates to a dextran sulfate, or a salt thereof, having a number average molecular weight ($M_n$) as measured by nuclear magnetic resonance (NMR) spectroscopy within an interval of 1850 and 3500 Da. The dextran sulfate, or the salt thereof, also has an average sulfate number per glucose unit within an interval of 2.5 and 3.0. Furthermore, an average sulfation of C2 position in the glucose units of the dextran sulfate, or the salt thereof, is at least 90%.

A dextran sulfate of the embodiments has improved biological effects and/or reduced toxicity as compared to similar dextran sulfate molecules available on the market.

BRIEF DESCRIPTION OF THE DRAWINGS

The embodiments, together with further objects and advantages thereof, may best be understood by making reference to the following description taken together with the accompanying drawings, in which:

FIG. 14 illustrates 2D $^{13}$C-1H HSQC spectrum of a dextran sulfate according to prior art.

DETAILED DESCRIPTION

Figure 1:
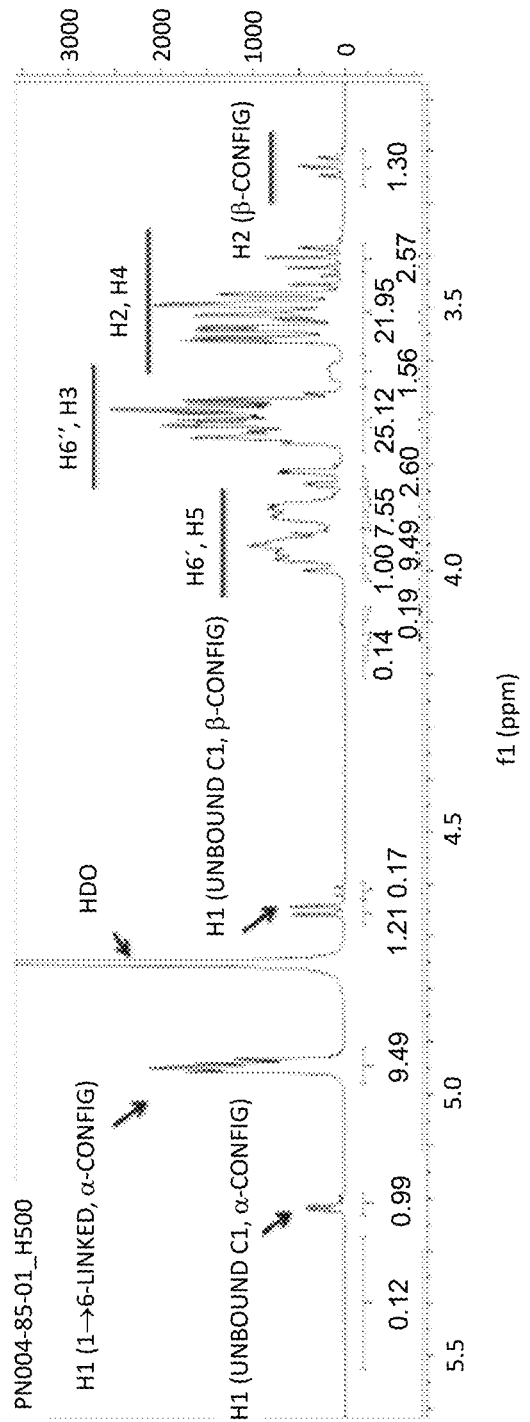
FIG. 1 is an expansion of 1D $^1$H NMR spectrum of the dextran starting material focused on the region with the dextran signals.

The present embodiments generally relate to dextran sulfate, and in particular to a new dextran sulfate having improved biological effect and low toxicity.

The present embodiments are based on the surprising discovery that dextran sulfate molecules have significantly different biological effects although the dextran sulfate molecules have rather similar chemical and physical properties. A dextran sulfate has thereby been manufactured having a number average molecular weight and sulfation content and pattern that result in improved biological effects and low toxicity as compared to similar dextran sulfate molecules available on the market.

Traditionally, dextran sulfate molecules have been characterized with regard to molecular weight parameters using size exclusion chromatography (SEC), such as SEC high-performance liquid chromatography (HPLC) or SE-HPLC for short. SEC is also known as gel filtration chromatography, gel permeation chromatography (GPC) or molecular sieve chromatography in the art. Other common technologies used to measure molecular weight parameters of dextran sulfate and related glucans is light scattering, such as static light scattering (SLS), or viscosity-based technologies.

However, these technologies of determining molecular weight parameters of dextran sulfate report on molecular volume and shape function rather than its molecular weight. This means that if the dextran sulfate molecules form aggregates or complexes during the measurements a higher apparent molecular weight is determined.

Furthermore, several factors and settings used in the measurement affect the apparent molecular weight of the dextran sulfate molecule, such as choice of chromatography column and eluent, flow rate settings, calibration procedure, including dextran standard used in the calibration procedure, charge of dextran sulfate molecules, etc.

In addition, the indirect methods rather report on molecular volume and shape, which may differ significantly not only from batch to batch but also from sample to sample within the same batch depending on, for instance, how the dextran sulfate material has been stored, how it is prepared prior to the measurement, etc.

A more exact technology has been used to determine molecular weight parameters of dextran sulfate that give true molecular weight parameters and not size-affected parameters. This technology is further compared to traditional used technologies mentioned above.

In order to be able to straight-forward compare molecular weight/size determinations by different methods, it is important to understand the commonly used molecular size definitions as listed here below. The parameter $N_i$ indicates the number of dextran sulfate molecules having a molecular weight of $M_i$ in a sample or batch.

Number average molecular weight ($M_n$):

$$\frac{\sum M_i N_i}{\sum N_i},$$

typically derived by end group assays, e.g. nuclear magnetic resonance (NMR) spectroscopy or chromatography. If a normal distribution is assumed, then a same number of dextran sulfate molecules can be found on each side of $M_n$, i.e. the number of dextran sulfate molecules in the sample having a molecular weight below $M_n$ is equal to the number of dextran sulfate molecules in the sample having a molecular weight above $M_n$.

Weight average molecular weight ($M_w$):

$$\frac{\sum M_i^2 N_i}{\sum M_i N_i},$$

typical for methods sensitive to molecular size rather than numerical value, e.g. light scattering and SEC methods. If a normal distribution is assumed, then a same weight on each side of $M_w$, i.e. the total weight of dextran sulfate molecules in the sample having a molecular weight below $M_w$ is equal to the total weight of dextran sulfate molecules in the sample having a molecular weight above $M_w$.

Average or size average molecular weights ($M_z$):

$$\frac{\sum M_i^{n+1} N_i}{\sum M_i^n N_i},$$

typical for methods measuring motion of molecules as diffusion techniques or sedimentation. Generally, more sensitive for high molecular weight polymers. Notably, n=0 gives $M_n$ and n=1 gives $M_w$.

Polydispersity index (PDI) ($M_w/M_n$), a common measure of the broadness of the molecular weight distribution. A value of 1 implies a monodisperse polymer, 1.02 to 1.10 is common for very controlled synthetic polymers, 1.5 to 2 are common for chain reaction products and ~2 is common for step polymerization products.

Mode of molecular weight distribution ($M_p$) represents molecular weight of highest peak in liquid chromatography (LC) chromatogram. Often stated for narrow distributions of standard polymers and determined by GPC/SEC or light scattering.

An aspect of the embodiments relates to dextran sulfate, or a salt thereof, characterized by a number average molecular weight ($M_n$) as measured by NMR spectroscopy within an interval of 1850 and 3500 Da.

The dextran sulfate, or the salt thereof, also has an average sulfate number per glucose unit within an interval of 2.5 and 3.0 and an average sulfation of C2 position in the glucose units of the dextran sulfate, or the salt thereof, is at least 90%.

The dextran sulfate, or the salt thereof, of the embodiments has a very narrow range of the molecular weight parameter values, i.e. the number average molecular weight ($M_n$). This number average molecular weight ($M_n$) is measured by an end group assay based on NMR spectroscopy as further described herein. NMR spectroscopy measurements give more consistent results with regard to molecular weight parameter determination than the traditionally used GPC, SEC and light scattering techniques. Furthermore, NMR spectroscopy measurements give true or correct number average molecular weight ($M_n$) of the dextran sulfate molecules that is not affected by any aggregation or complex formation, which is a common problem in the traditionally used techniques.

In a particular embodiment, the dextran sulfate, or the salt thereof, has a number average molecular weight ($M_n$) as measured by NMR spectroscopy within an interval of 1850 and 2500 Da, preferably within the interval of 1850 and 2300 Da. In a particular embodiment, the dextran sulfate, or the salt thereof (excluding any counter ions), has a number average molecular weight ($M_n$) as measured by NMR spectroscopy within an interval of 1850 and 2200 Da, preferably within an interval of 1850 and 2100 Da and more preferably within an interval of 1850 and 2000 Da.

In an embodiment, the salt of dextran sulfate is a sodium salt or a potassium salt, preferably a sodium salt. The salt is preferably a pharmaceutically acceptable salt of dextran sulfate.

In a particular embodiment, the sodium salt of dextran sulfate including the Na⁺ counter ions has a number average molecular weight ($M_n$) as determined by NMR spectroscopy within an interval of 1850 and 3500 Da, preferably within an interval of 2000 and 2500 Da and more preferably within an interval of 2000 and 2400 Da, such as within an interval of 2100 and 2300 Da.

In an embodiment, the dextran sulfate, or the salt thereof, preferably has an average number of glucose units within an interval of 4.0 and 6.0. In a preferred embodiment, the dextran sulfate, or the salt thereof, has an average number of glucose units within an interval of 4.5 and 5.5, more preferably within an interval of 5.0 and 5.2, such as about 5.1.

In an embodiment, the dextran sulfate, or the salt thereof, has an average sulfate number per glucose within an interval of 2.5 and 2.8, preferably within an interval of 2.6 and 2.7.

An average number of glucose units within an interval of 4.0 and 6.0 and an average sulfate number per glucose unit within an interval of 2.5 and 3.0 result in a total number of sulfate atoms in the dextran sulfate, or the salt thereof, within an interval of 10.0 and 18.0. In an embodiment, the dextran sulfate, or the salt thereof, preferably has a total number of sulfate atoms within an interval of 11.25 and 15.4, preferably within an interval of 13.0 and 14.0.

Generally, a dextran sulfate molecule of the embodiments having on average 5.1 glucose units and an average sulfate number per glucose unit of 2.6 to 2.7 typically result in a number average molecular weight ($M_n$) as measured by NMR spectroscopy within an interval of 1850 and 2000 Da.

The formula below schematically represents a dextran sulfate molecule with three glucose units and a maximum number of sulfur atoms, i.e. each site or position in the dextran core that can be sulfated has been sulfated in the structural formula. Hence, the non-end glucose unit is illustrated as being sulfated at C2, C3 and C4 positions and the end glucose unit with free C1 position is sulfated at C1, C2, C3 and C4 positions and the end glucose unit with free C6 position is sulfated at C2, C3, C4 and C6 positions.

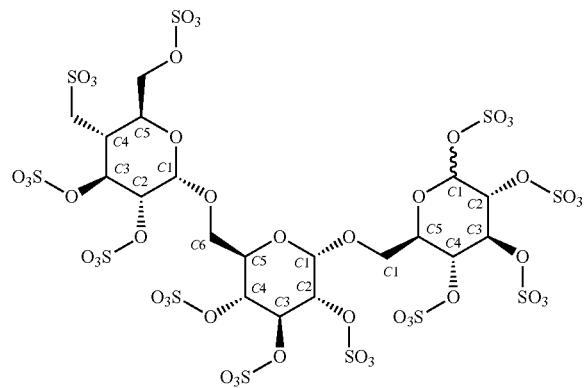

The average sulfatation of the C2 position in the glucose units of the dextran sulfate, or the salt thereof, is at least 90%. In an embodiment, the average sulfation of the C2 position is at least 95%.

In an embodiment, the average sulfate number at the C2, C3 and C4 positions in the glucose units of the dextran sulfate, or the salt thereof, is within an interval of 2.0 and 2.6, preferably within an interval of 2.2 and 2.6, such as within an interval of 2.3 and 2.5. In an embodiment, the average sulfation of the C3 position in the glucose units of the dextran sulfate, or the salt thereof, is within an interval of 80 and 90%, preferably within an interval of 84 and 87%.

The dextran sulfate, or the salt of the embodiments, thereby has a high degree of sulfation at the C2, C3 and C4 positions in the glucose units in the dextran core. In a particular embodiment, at least 70% of these positions are sulfated and more preferably at least 75% of these positions. In a particular embodiment, 75 to 85% of the total number of the C2, C3 and C4 positions in the dextran core are sulfated.

In an embodiment, an average sulfation of the end group C6 is at least 80%, preferably at least 85%.

The end group C1 can assume an α-configuration or a β-configuration. Generally there is an equilibrium between these two end group configurations.

It seems that the end group C1 is more easily sulfated when assuming the β-configuration as compared to the α-configuration. Hence, in a particular embodiment, the sulfation of the end group C1 is higher when in the β-configuration as compared to the α-configuration. In an embodiment, an average sulfation of the end group C1 in β-configuration is at least 75%, preferably at least 80% or at least 85%. Correspondingly, in an embodiment, an average sulfation of the end group C1 in α-configuration is preferably at least 15%, preferably within an interval of 15 and 75%, more preferably within an interval of 15 and 50%, such as within an interval of 15 and 45%.

In an embodiment, an end group C1 position is sulfated or is bond to —OH. Hence, the dextran sulfate, or the salt thereof, preferably lacks any end terminal modification other than sulfation (—SO₃).

As mentioned in the background, the straight chain of dextran consists of α-1,6 glycosidic linkages between glucose units. The dextran molecule could be a straight chain merely consisting of glucose units in a non-branched chain. Dextran molecules could also be branched, usually through α-1,3 linkages.

In an embodiment, the dextran sulfate, or the salt thereof, has an average branching of glucose units that is less than 5.0%, such as less than 3.0%, preferably less than 1.5%, such as less than 1.0%. Hence, the dextran sulfate, or the salt thereof, of the embodiments is preferably a highly straight molecule with few branches if any.

A particular embodiment relates to a sodium salt of dextran sulfate having a number average molecular weight ($M_n$) as measured by NMR spectroscopy, including the Na⁺ counter ion, within an interval of 2100 and 2300 Da. The salt of dextran sulfate has on average 5.0 to 5.2 glucose units and an average sulfate number per glucose unit is within an interval of 2.5 and 2.8. In a particular embodiment, the average sulfation of the C2 position is at least 95%. An average sulfate number at the C2, C3 and C4 positions in the glucose units is furthermore preferably within an interval of 2.2 and 2.6.

The dextran sulfate of the embodiments has improved biological effects and/or lower toxicity as compared to similar dextran sulfate molecules available on the market as shown in the following experiments. These differences in biological effects and toxicity were highly surprising given that the dextran sulfate molecules have fairly similar molecular weight and sulfation parameters. Hence, there seems to be specific ranges of molecular parameter values and sulfation parameter values that give the dextran sulfate molecules these advantageous effects over other dextran sulfate molecules having molecular weight parameter values and/or sulfation parameter values outside of the specific ranges or intervals of the embodiments.

Dextran sulfate is produced by sulfation of a dextran starting material in an esterification reaction. There are various production processes disclosed in the prior art for the production of dextran sulfate. Examples of documents that disclose such production processes include Ricketts, *Biochemical Journal*, 51: 129-133 (1952); Swedish patent no. 165 090; U.S. Pat. Nos. 2,715,091; 3,141,014; 3,498,972 and 4,855,416. Different production processes use different sulfating agent, such as concentrated sulfuric acid ($H_2SO_4$), sulfur trioxide ($SO_3$) or chlorosulfonic acid ($ClSO_3H$); different solvents, such as pyridine ($C_5H_5N$), formamide ($NH_2COH$), or acetamide ($CH_3CONH_2$); and different process parameters. These differences may influence the chemical and physical properties of the dextran sulfate end product.

Figure 12:
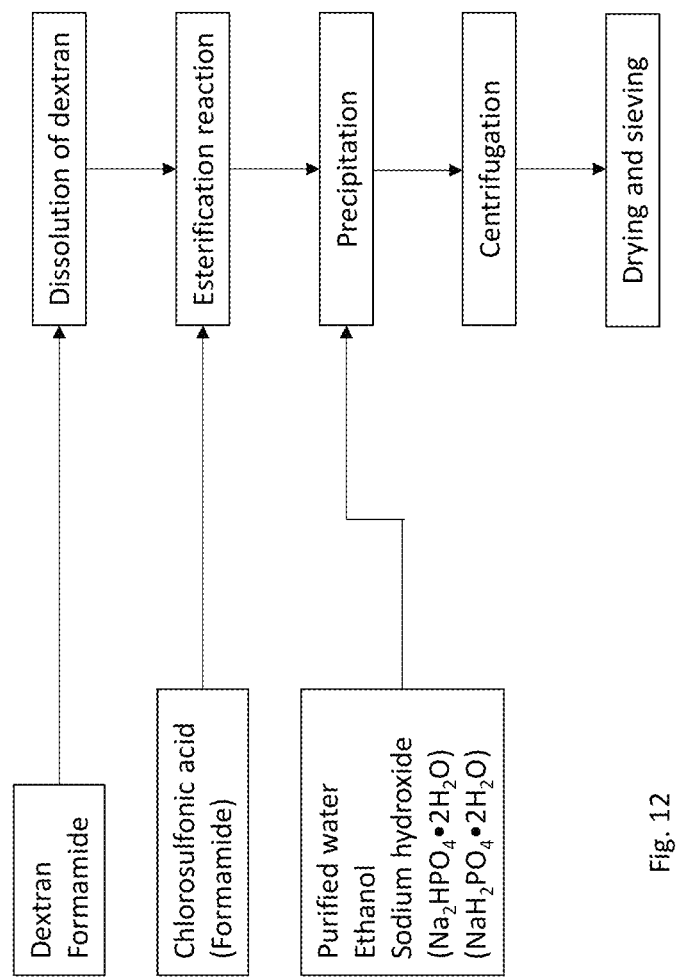
FIG. 12 is a flow chart illustrating a production process for the production of dextran sulfate of the embodiments.

A currently preferred production process is described here below with reference to FIG. 12. Dextran sulfate is produced by sulfating a dextran starting material. Separation of dextran sulfate with appropriate molecular weight is accomplished by ethanol fractionation, in which the largest molecular weight molecules precipitates first.

In a first step, the dextran starting material is added to the solvent formamide under stirring. The vessel content is stirred and gently heated, then cooled as the mixture is transferred to the scrubber.

In the esterification reaction, chlorosulfonic acid is added during 5-6 hours under cooling with brine. The temperature is kept constant ≤34° C., and if needed, heated with 1 atm pressure water vapor. The mixture is transferred to another vessel via the scrubber followed by a rinse with purified water. Stirring is made before the first ethanol precipitation.

In an alternative embodiment, the cholorosulfonic acid is added to a portion of the formamide during about 3 hours under cooling with brine. The mixture of dextran and the remaining formamide is then transferred to the vessel containing the mixture of chlorosulfonic acid and formamide while maintaining the temperature ≤34° C.

In the precipitation step, an ethanol-water mixture is pumped to the dextran sulfate mixture, which is stirred. The mixture is left overnight under cooling with brine. On the next day, the top phase, supernatant (ethanol phase) is removed. The lower phase is washed with ethanol, stirred, left to precipitate, and the supernatant is removed. This procedure is conducted five times. Cooling is achieved with brine and sodium hydroxide is added until the pH is 9.5. After the second and fourth precipitation step, the precipitate is dissolved with water. After the third precipitation step, the precipitate is dissolved in water and optionally disodium hydrogen phosphate and sodium dihydrogen phosphate. The fifth precipitation step is conducted with absolute ethanol. The dextran sulfate mixture is pumped through a filter to an ethanol vessel, under cooling with brine or cooling water (at approximately 10° C.). The pump is rinsed with purified water, stirred, and left for sedimentation. The ethanol supernatant is removed to a tank and absolute ethanol is added to the product under stirring. The mixture is cooled with cooling water.

The above description precipitation procedure is a preferred procedure within the production of a dextran sulfate according to the embodiments. However, variants of the precipitation procedure are possible, such as reducing or increasing the number of precipitation steps. Although ethanol is a preferred alcohol used in the precipitation procedure, other alcohols could be used, such as methanol.

In the centrifugation step, the mixture is moved to a centrifuge. After the centrifugation, the centrifugate is removed. It is placed in plastic containers lined with double plastic bags. The centrifugate is dissolved in ethanol. Then it is centrifuged once more, and the centrifugate is washed with ethanol in the centrifuge.

The centrifugate is put in filter covered beakers in LAF 5, and then the beakers are placed in a vacuum drying cabinet. After drying the dextran sulfate powder is passed through a 710 μm sieve into plastic containers lined with PE bags.

In order to produce about 10-13 kg of dextran sulfate of the embodiments the following materials and amounts are typically used.

| Component | Formula | Amount (kg) |
|---|---|---|
| Dextran 1 (Pharmacosmos A/S) | $(C_6H_{10}O_6)_n$ | 9.2 |
| Formamide (Univar A/S) | $NH_2COH$ | 69.4 |
| Chlorosulfonic acid (Merck-Schuchardt) | $ClSO_3H$ | 25.8 |
| Sodium hydroxide 27.7% (Chemark) | $NaOH$ | 20.7 |
| Purified water | $H_2O$ | |
| Ethanol (Univar A/S) | $C_2H_5OH$ | 135 |
| Disodium hydrogen phosphate dihydrate (Merck) | $Na_2HPO_4 \cdot 2H_2O$ | 0.2493 |
| Sodium dihydrogen phosphate dihydrate (Merck) | $NaH_2PO_4 \cdot 2H2O$ | 0.2144 |
| Product | | |
| Sodium dextran sulfate | $(C_6H_{10}O_6)_n\text{—}SO_3^-Na^+$ | ~10-13 |

Main Reaction During Synthesis:

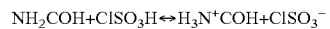

$$NH_2COH + ClSO_3H \leftrightarrow H_3N^+COH + ClSO_3^-$$

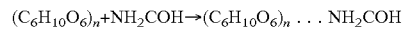

$$(C_6H_{10}O_6)_n + NH_2COH \rightarrow (C_6H_{10}O_6)_n \ldots NH_2COH$$

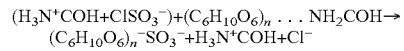

$$(H_3N^+COH + ClSO_3^-) + (C_6H_{10}O_6)_n \ldots NH_2COH \rightarrow (C_6H_{10}O_6)_n\text{-}SO_3^- + H_3N^+COH + Cl^-$$

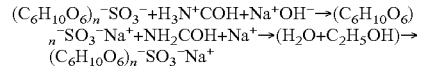

$$(C_6H_{10}O_6)_n\text{-}SO_3^- + H_3N^+COH + Na^+OH^- \rightarrow (C_6H_{10}O_6)_n\text{-}SO_3^-Na^+ + NH_2COH + Na^+ \rightarrow (H_2O + C_2H_5OH) \rightarrow (C_6H_{10}O_6)_n\text{-}SO_3^-Na^+$$

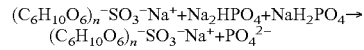

$$(C_6H_{10}O_6)_n\text{-}SO_3^-Na^+ + Na_2HPO_4 + NaH_2PO_4 \rightarrow (C_6H_{10}O_6)_n\text{-}SO_3^-Na^+ + PO_4^{2-}$$

Another aspect of the embodiments relates to a dextran sulfate according to the embodiments for use as a medicament.

Further aspect of the embodiments relates to a dextran sulfate according to the embodiments for use in different medical applications including for use in mobilizing progenitor and/or stem cells into the peripheral blood of a subject, including mobilization of hematopoietic stem cells (HSCs) and/or mesenchymal stem cells (MSCs); for use in mobilizing target white blood cells, in particular lymphocytes, into the blood stream of a subject; for use in reducing pulmonary uptake of intravenously injected cells in a subject; for use in inducing hepatocyte growth factor (HGF) in a subject, and for use as an anticoagulant. The dextran sulfate according to the embodiments is also suitable for use in treating, inhibiting or preventing various demyelinating diseases, including CNS demyelinating diseases, such as myelinoclastic disorders, e.g. multiple sclerosis (MS) and Devic's disease, acute disseminated encephalomyelitis (ADEM), leukodystrophic disorders, e.g. CNS neuropathies, central pontine myelinolysis, myelopathies, leukoencephalopathies and leukodystropies, and peripheral demyelinating diseases, such as Guillain-Barre syndrome, chronic inflammatory demyelinating polyneuropathy and peripheral neuropathies.

The dextran sulfate of the embodiments can also be useful in treating, inhibiting and/or preventing instant blood-mediated inflammatory reaction (IBMIR) and graft rejection of organs, tissues and in particular cell implants, such as islets of Langerhans.

Dextran sulfate, or the pharmaceutically acceptable salt thereof, of the embodiments is preferably administered by injection to the subject and in particular by intravenous (i.v.) injection, subcutaneous (s.c.) injection or (i.p.) intraperitoneal injection, preferably i.v. or s.c. injection. Other parenteral administration routes that can be used include intramuscular and intraarticular injection.

The dextran sulfate, or the pharmaceutically acceptable salt thereof, of the embodiments is preferably formulated as an aqueous injection solution with a selected solvent or excipient. The solvent is advantageously an aqueous solvent and in particular a buffer solution. A non-limiting example of such a buffer solution is a citric acid buffer, such as citric acid monohydrate (CAM) buffer, or a phosphate buffer.

For instance, dextran sulfate of the embodiments can be dissolved in saline, such as 0.9% NaCl saline, and then optionally buffered with 75 mM CAM and adjusting the pH to about 5.9 using sodium hydroxide. Also non-buffered solutions are possible, including aqueous injection solutions, such as saline, i.e. NaCl (aq). Furthermore, other buffer systems than CAM or phosphate buffer could be used if a buffered solution are desired.

The embodiments are not limited to injections and other administration routes can alternatively be used including orally, nasally, bucally, rectally, dermally, tracheally, bronchially, or topically. The active compound, dextran sulfate, is then formulated with a suitable excipient or carrier that is selected based on the particular administration route.

Suitable dose ranges for the dextran sulfate of the embodiments may vary according to the size and weight of the subject, the condition for which the subject is treated, and other considerations. In particular for human subjects, a possible dosage range could be from 1 µg/kg to 150 mg/kg of body weight, preferably from 10 µg/kg to 100 mg/kg of body weight.

In preferred embodiments, the dextran sulfate, or the pharmaceutically acceptable derivative thereof, is formulated to be administered at a dosage in a range from 0.05 to 50 mg/kg of body weight of the subject, preferably from 0.1 to 40 mg/kg of body weight of the subject, and more preferably from 0.1 to 30 mg/kg or from 0.1 to 15 mg/kg body weight of the subject.

Administration of dextran sulfate, or the pharmaceutically acceptable salt thereof, does not necessarily have to be limited to treatment of a present medical condition but could alternatively, or in addition, be used for prophylaxis.

The dextran sulfate of the embodiments can be administered at a single administration occasion, such as in the form of a single bolus injection. This bolus dose can be injected quite quickly to the patient but is advantageously infused over time so that the dextran sulfate solution is infused over a few minutes of time to the patient, such as during 5 to 10 minutes.

Alternatively, dextran sulfate of the embodiment can be administered at multiple, i.e. at least two, occasions during a treatment period. Generally, for acute diseases, the duration of the treatment period could be a single administration but is preferably in the form of several administrations during a treatment period of, for instance, a week, a few weeks, or a month. Longer treatment periods up to three months or even a year can further improve healing and recovery.

The subject is an animal subject, preferably a mammalian subject and more preferably a human subject.

EXPERIMENTS

Characterization of Dextran and Dextran Sulfate

The primary study aim is to characterize the new dextran sulfate and compare physical and chemical differences between the dextran sulfate as compared to other similar dextran sulfate molecules.

NMR Spectroscopy

A 500 MHz Varian Inova spectrometer equipped with a 5 mm $^1$H/$^{13}$C/$^{15}$N triple resonance probe was used in the performed NMR experiments. The following types of spectra were recorded using standard versions of 1D $^1$H, 2D $^1$H gradient-COSY (correlation spectroscopy), $^1$H-$^{13}$C HSQC (heteronuclear single quantum coherence spectroscopy), $^1$H-$^{13}$C HMBC (heteronuclear multiple-bond correlation spectroscopy) and 2D $^1$H-$^1$H ROESY (rotating frame nuclear Overhauser effect spectroscopy) with adiabatic spin-lock corresponding to a 200 millisecond mixing time. A 400 MHz Varian Inova spectrometer equipped with a 5 mm $^1$H/$^{13}$C switchable gradient probe ($^{13}$C inner coil) was used for recording 1D $^{13}$C spectra. Spectra were recorded at room temperature (25° C.). Quantitative 1D $^1$H NMR spectra was acquired using a total relaxation delay between the scans of 60 seconds with an acquisition time of 3 seconds and a spectra width of 14.5 ppm. The residual HDO signal was referenced to 4.75 ppm in the $^1$H dimension while indirect chemical shift referencing was used in the $^{13}$C dimension using the gyromagnetic ratios of $^{13}$C and $^1$H.

All NMR spectra were processed and analyzed with MestreNova 9.0.0. Processing of the 1D $^1$H spectra was performed using a 1 Hz Lorentzian line broadening and base line correction (automatic Whitaker or a polynomial function of order 3). Integration was performed using the "peak mode" of MestreNova of 1D spectra using the following regions as reporters for various structural elements:

| Area (ppm range) | Atoms of interest in area (peaks may or may not be present) |
| --- | --- |
| 6.11 . . . 5.93 | sulfated end C1 in α-configuration |
| 5.63 . . . 5.50 | non-sulfated end C1 in α-configuration next to sulfated C2 |
| 5.43 . . . 5.22 | non-end C1 next to sulfated C2 + non-sulfated end C1 in α-configuration next to non-sulfated C2 |
| 5.17 . . . 4.87 | non-end C1 next to non-sulfated C2 + sulfated end C1 in β-configuration |
| 4.70 . . . 3.54 | C2-C6 (both sulfated and non-sulfated) |

Figure 5:
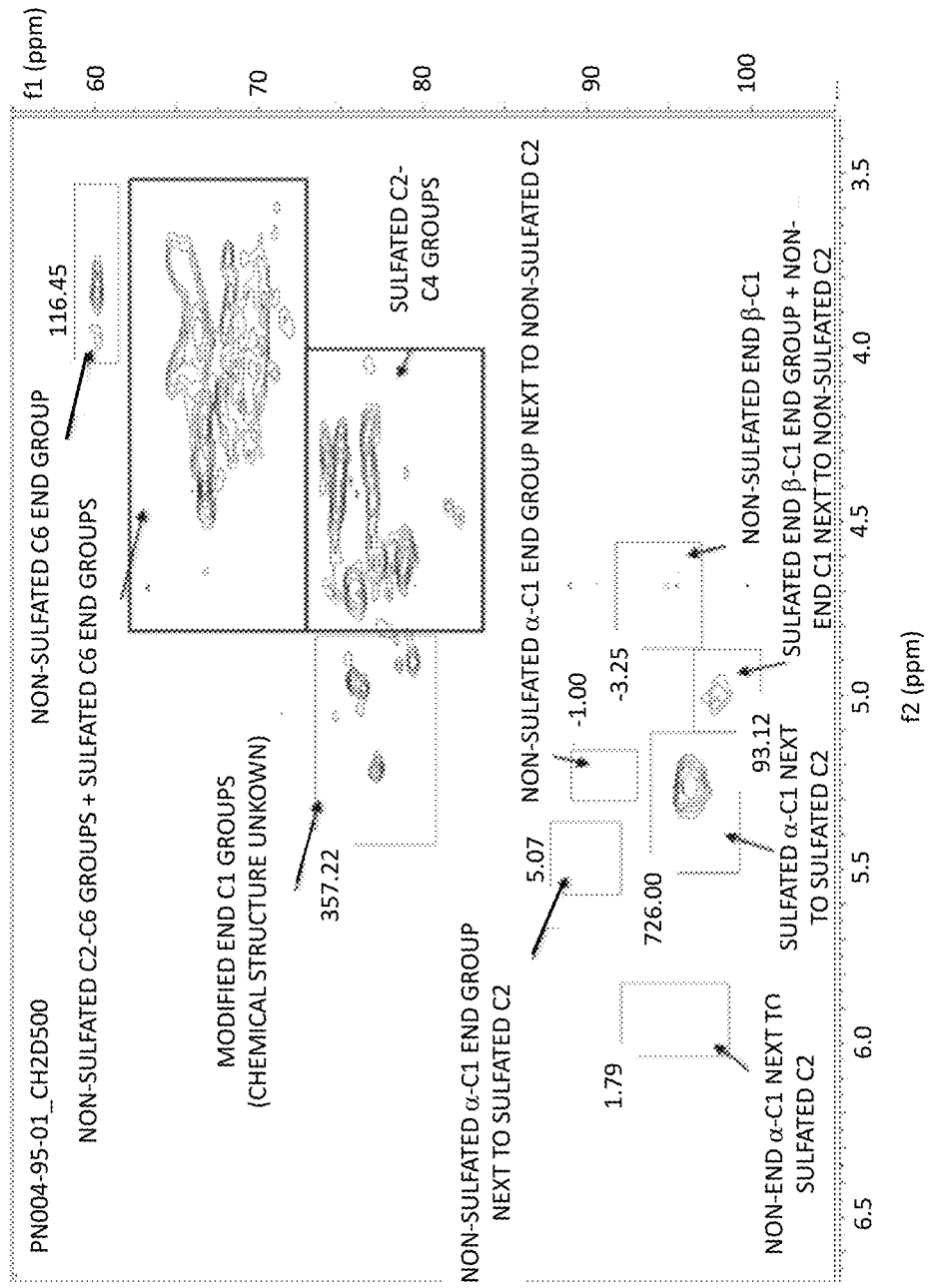
FIG. 5 illustrates 2D $^{13}$C-$^1$H HSQC spectrum of a dextran sulfate of the embodiments (batch no. 3) at 25° C. Each peak corresponds to a C—H bond with different chemical environment. Peak areas are approximately proportional to the population of each C—H bond.

2D HSQC spectra were subjected to pure sine square functions in both dimensions, and integration of selected rectangular spectral areas, see FIG. 5, was performed.

| | $^1$H chemical shift range | $^{13}$C chemical shift range |
|---|---|---|
| H1/C1 group | 6.30-4.40 ppm | 105.2-86.2 ppm |
| Sulfated H2/C2, H3/C3, H4/C4 | 4.84-3.77 ppm | 85.4-73.0 ppm |
| H5/C5, H6/C6 and non-sulfated H2/C2, H3/C3, H4/C4 (2 areas) | 4.56-3.08 ppm | 72.6-58.3 ppm |
| | 3.77-3.08 ppm | 77.8-72.6 ppm |

NMR Chemicals and Materials

| Name | Code no | Batch | D-purity | Supplier |
|---|---|---|---|---|
| D$_2$O | 166301000 | A0319250 | 99.8% | Acros Organics, CAS 7789-20-0 |
| D$_2$O | 151882-1006 | STBD4348V | 99.9% | Sigma Aldrich, CAS 7789-20-0 |

Wilmad NMR tubes, 5 mm diameter, Z565229-100EA, batch 3110

Experiment Validation

In order to assess the performance of the NMR-based end group assay, 1D $^1$H NMR experiments were performed on a set of commercially available dextran molecular weight standards using a parameter set for fully quantitative analyses (recycle delay of 60 s). Notably, dextran standards are commonly also used as standards for molecular size determination of dextran sulfate since no dextran sulfate molecular size standards are commercially available.

Dextran Standard 1000 (product no. 31416, Fluka, batch no. BCBM6794V, CAS no. 9004-54-0) obtained from *Leuconostoc mesenteroides*; Analytical standard for GPC, M$_w$ 1000 Da.

Dextran Standard 5000 (product no. 31417, Fluka, batch no. BCBL9398V, CAS no. 9004-54-0) obtained from *Leuconostoc mesenteroides*; Analytical standard for GPC, M$_w$ 5000 Da.

Dextran Standard 12000 (product no. 31418, Fluka, batch no. BCBN0032V, CAS no. 9004-54-0) obtained from *Leuconostoc mesenteroides*; Analytical standard for GPC, M$_w$ 12000 Da.

Table 1 below compares the M$_n$ values (in Da) obtained from the NMR spectroscopy measurements with the M$_n$ values obtained from the supplier. The table also lists M$_w$ and M$_p$ values (in Da) as obtained from the supplier.

TABLE 1

| molecular weight parameters for dextran standards | | | | | |
|---|---|---|---|---|---|
| Dextran standard | M$_n$ (NMR) | M$_n$ (supplier) | M$_w$ (supplier) | PDI | M$_p$ (supplier) |
| 1000 | 1055 | 1010 | 1270 | 1.26 | 1080 |
| 5000 | 2850 | 3260 | 5220 | 1.60 | 4440 |
| 12000 | 8105 | 8110 | 11600 | 1.43 | 9890 |

There is good agreement between the M$_n$ values as measured using NMR spectroscopy with the data obtained from the supplier. The M$_n$ values measured by NMR spectroscopy corresponds to 6.4, 17.4 and 49.9 glucose units, respectively, for the three dextran standards.

NMR Characterization of Dextran Starting Material

An NMR spectroscopy study was conducted on the dextran starting material used to produce dextran sulfate of the embodiments. The dextran (Pharmacosmos, Dextran 1, batch no. 345349) is produced by the enzyme dextran sucrose from *Leuconostoc mesentoroides* B512F.

An NMR sample of the dextran was prepared in D$_2$O and analyzed in detail by 2D $^1$H/$^{13}$C NMR spectroscopy. Almost complete $^1$H/$^{13}$C chemical shift assignment was obtained from a set of 2D NMR spectra acquired at 25° C. in D$_2$O, see Table 2. The results indicate that the dextran is essentially unbranched, i.e. almost exclusively consisting of glucose rings linked together with α-(1→6)-glycoside bonds. No α-(1→3)-glycoside branching could be observed, implying that any such branching is lower than 0.5%. Furthermore, the data shows that the overall branching is <1% including α-(1→2)-, α-(1→3)- and α-(1→4)-branching.

TABLE 2

$^1$H and $^{13}$C chemical shift assignment of Dextran 1 (25° C., D$_2$O)

| | Relative intensity | | Chemical shifts (ppm) | | | | | |
|---|---|---|---|---|---|---|---|---|
| | | | 1 | 2 | 3 | 4 | 5 | 6 |
| Middle glucose unit (unbranched) α(1→6) × 2 | 58% | $^1$H | 4.95 | 3.55 | 3.70 | 3.49 | 3.89 | 3.95, 3.74 |
| | | $^{13}$C | 97.7 | 71.3 | 73.2 | 69.5 | 70.1 | 65.5 |
| C1-terminal glucose unit with β-configuration of C1 | 12% | $^1$H | 4.65 | 3.23 | 3.46 | 3.62 | 3.50 | 3.94 |
| | | $^{13}$C | 96.0 | 74.0 | 75.9 | 74.1 | 69.4 | 65.5 |
| C1-terminal glucose unit with α-configuration of C1 | 8% | $^1$H | 5.21 | 3.51 | 3.68 | 3.49 | 3.99 | 3.99, 3.68 |
| | | $^{13}$C | 92.1 | 69.9 | 72.9 | 69.5 | 69.9 | 65.7 |
| C6-terminal glucose unit with α-configuration of C1 | 22% | $^1$H | 4.94 | 3.53 | 3.69 | 3.40 | 3.69 | 3.83, 3.74 |
| | | $^{13}$C | 97.6 | 71.3 | 71.8 | 69.4 | 73.0 | 60.4 |
| Unidentified spin system | <0.1% | $^1$H | 5.30 | | | | | |
| | | $^{13}$C | 99.2 | | | | | |

Notably, the terminal glucose ring with a free anomeric carbon (C1 terminal ring) exists both in the α-configuration (42%) and β-configuration (58%) as based on the observed $^1$H/$^{13}$C chemical shifts. The average number of glucose units in each dextran molecule is determined to be 5.1 glucose units using the integral values of the various H1 groups in the 1D $^1$H spectrum and the average molecular weight was determined to be 852 Da. The degree of branching was determined to be less than 1%. FIG. 1 illustrates an expansion of 1D $^1$H spectrum focused on the region with the dextran signals.

NMR Characterization of Dextran Sulfate

In the present study, three batches (batch nos. 1, 2 and 3) of the dextran sulfate of the embodiments where compared to three dextran sulfate products obtained from TdB Consultancy: dextran sulfate 5 LS (product no. DB005, batch no. 20288, low sulfated, molecular weight 5 kDa), dextran sulfate 5 HS (product no. DB004, batch nos. 20281 and 20300, high sulfated, molecular weight 5 kDa) and dextran sulfate 3 (batch no. 20341, high sulfated, molecular weight 3 kDa).

NMR Samples

| | |
|---|---|
| PN004-83-01 | The NMR sample was prepared by dissolving 33.91 mg of batch no. 1 of dextran sulfate of the embodiments in 500 μl D$_2$O. |
| PN004-83-02 | The NMR sample was prepared by dissolving 49.80 mg of batch no. 2 of dextran sulfate of the embodiments in 500 μl D$_2$O. |
| PN004-83-03 | The NMR sample was prepared by dissolving 35.45 mg of batch no. 3 of dextran sulfate of the embodiments in 500 μl D$_2$O. |
| PN004-95-01 | The NMR sample was prepared by dissolving 34 mg of dextran sulfate 3 from TdB Consultancy AB (batch no. 20341) in 520 μl D$_2$O. |
| PN004-95-02 | The NMR sample was prepared by dissolving 54.4 mg of dextran sulfate 5 LS from TdB Consultancy AB (batch no. 20228) in 520 μl D$_2$O. |
| PN004-33-03 | The NMR sample was prepared by dissolving 54.4 mg of dextran sulfate 5 HS from TdB Consultancy AB (batch no. 20281) in 520 μl D$_2$O. |
| PN004-33-02 | The NMR sample was prepared by dissolving 54.4 mg of dextran sulfate 5 HS from TdB Consultancy AB (batch no. 20300) in 520 μl D$_2$O. |

General NMR Comments

Figure 2:
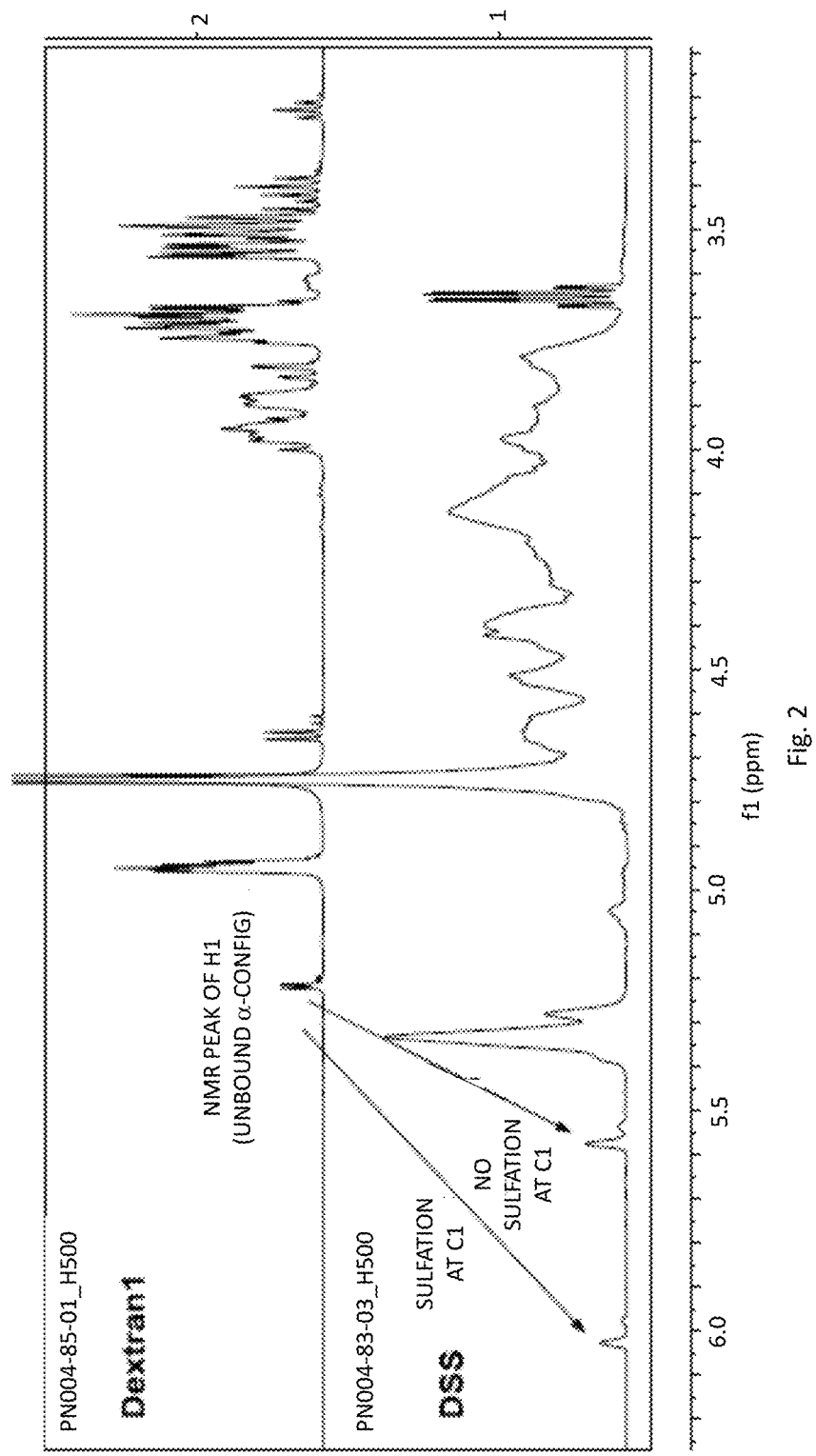
FIG. 2 is a comparison of 1D $^1$H NMR spectra of the dextran starting material and a dextran sulfate of the embodiments (batch no. 3).

Dextran sulfate consists of a distribution of similar but non-identical molecules with various sulfate patterns, branching and sizes as well as differences in end group configuration and chemistry. This results in challenging structural analyses. NMR spectra of dextran sulfate are complex, see FIG. 2 illustrating a comparison of 1D $^1$H NMR spectra of the dextran starting material and dextran sulfate. For this reason, it may be necessary to also use quantitative data from 2D spectra although the quantitative performance of 2D NMR normally is less accurate and precise as compared with quantitative 1D $^1$H NMR techniques.

Few NMR publications exist with respect to this topic (Neville et al., *J. Pharm. Sci.*, 80(3): 239-244 (1991) and Ludwig-Baxter et al., *J. Pharm. Sci.*, 80(7): 655-660 (1991)). In sulfated glucose, the $^1$H chemical shifts are in general shifted downfield (higher chemical shifts) increasingly with the distance to each introduced sulfate group. On the other hand, the $^{13}$C chemical shifts behave differently and the effect is depending on how many covalent bonds are between the carbon and the sulfate group(s). The $^{13}$C chemical shift of a carbon increases with 4-10 ppm if the sulfate is linked to that carbon while if a sulfate is bound to an adjacent carbon, the chemical shift effect is smaller but opposite. For sulfate groups linked to carbons further away, the effect is normally minute. Similar effects on $^{13}$C chemical shifts are expected upon branching. In summary, $^{13}$C chemical shifts are more useful reporters as they mainly are dependent on local geometry such as dihedral angles as well as nearby covalently bound atom types (typically 2-4 bonds apart).

End-Group Characterization

Compared with dextran, the NMR spectra of dextran sulfate are more complex due to the significantly increased number of NMR signals originating from various chemical environments for all combinations of sulfated/non-sulfated C2, C3 and C4 as well as the C1 and C6 end groups.

The C1 end groups (free anomeric carbon) are more readily analyzed than the C6 end groups due to the spectral characteristics even if the C1 end group is complicated by, for example, overlap between the peaks of the sulfated C1 in β-configuration and the non-end group C1 without sulfated C2. The large residual water signal located in the C1 region of the 1H spectra also complicates the analyses.

Figure 3:
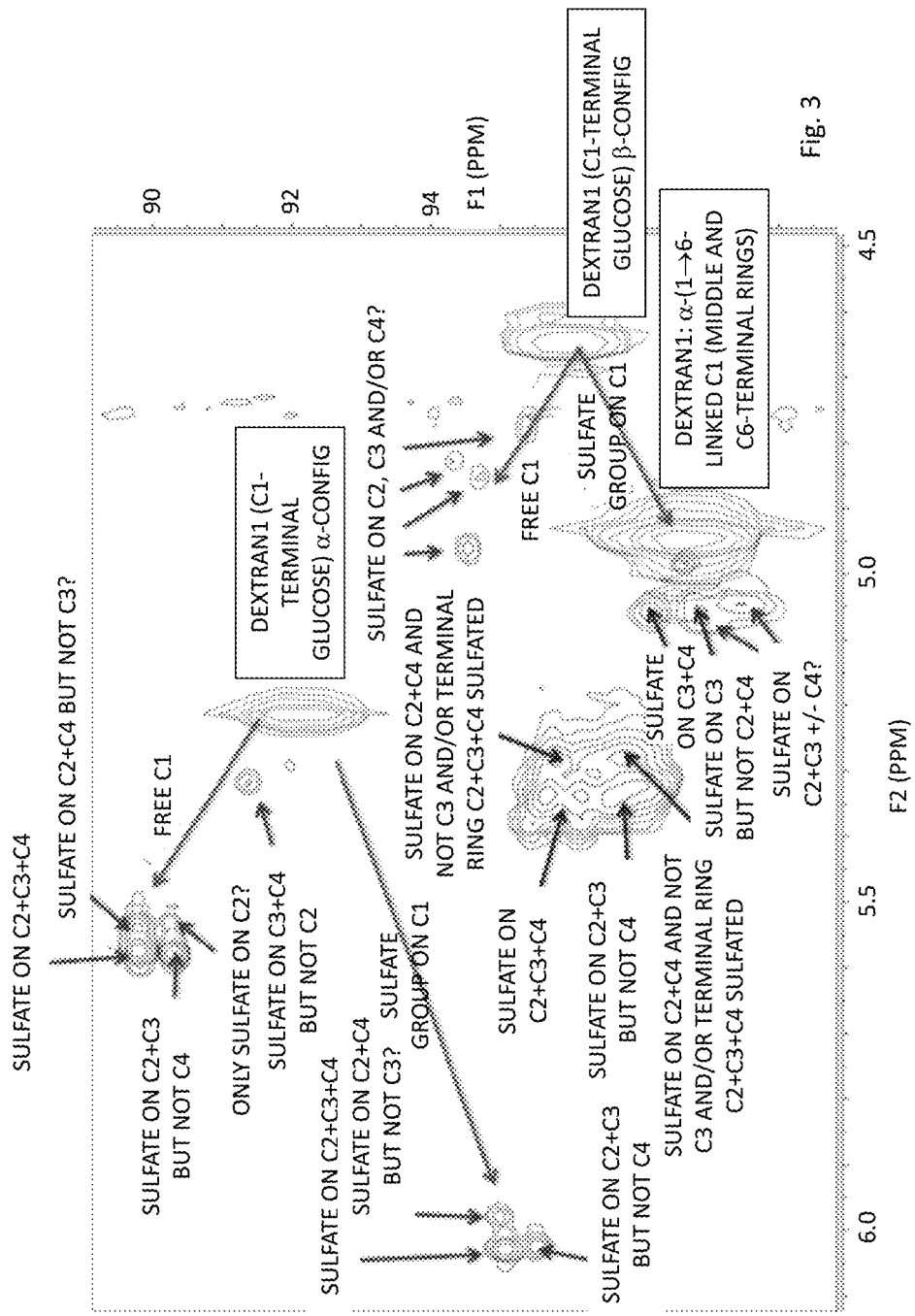
FIG. 3 illustrates 2D $^{13}$C-$^1$H HSQC spectrum of a dextran sulfate of the embodiments (batch no. 1) at 25° C. overlaid with the corresponding spectrum of the dextran sulfate starting material.

FIG. 3 illustrates a 2D $^{13}$C-$^1$H HSQC spectrum of dextran sulfate from batch no. 1 at 25° C. overlaid with the corresponding spectrum of the dextran starting material (Dextran1). The figure illustrates the tentative assignment of each H1/C1 group to a specific sulfation state. The figure indicates peaks belonging to the C1-terminal glucose unit and peaks belonging to the abundant middle and C6-terminal glucose rings.

Effects due to possible sulfation of C6 in C6-terminal glucose rings are neglected.

Figure 4:
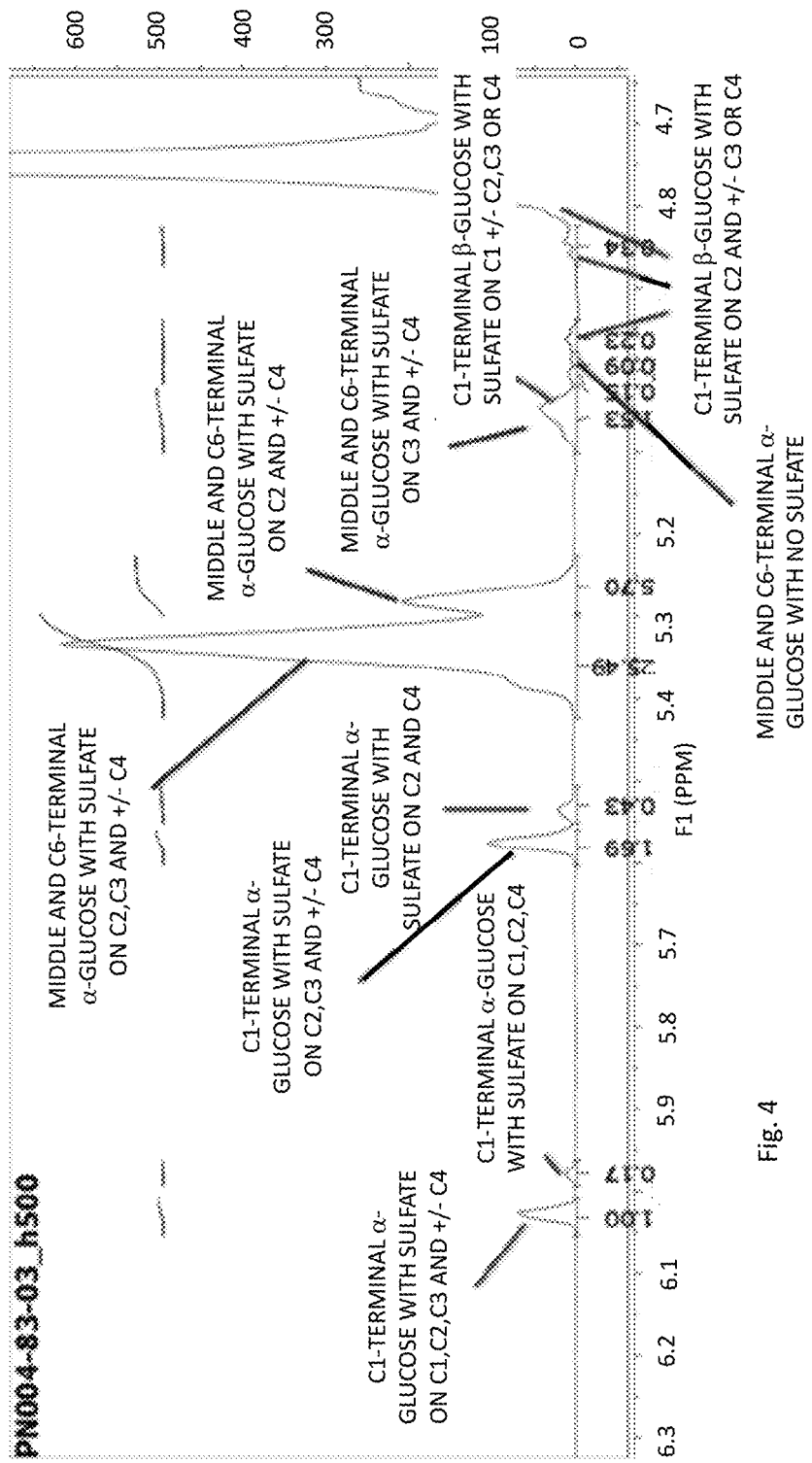
FIG. 4 illustrates 1D $^1$H NMR spectrum of a dextran sulfate of the embodiments (batch no. 3) at 25° C.

FIG. 4 illustrates 1D $^1$H NMR spectrum of dextran sulfate from batch no. 3 at 25° C. This figure illustrates the tentative assignment of each H1 peak to a specific sulfation state. The figure indicates peaks belonging to the C1-terminal glucose unit and peaks belonging to the abundant middle and C6-terminal glucose rings. The assignment is tentative in particular with respect to sulfation of C3 and C4 and those effects due to possible sulfation of C6 in C6-terminal glucose rings are neglected.

Figure 6:
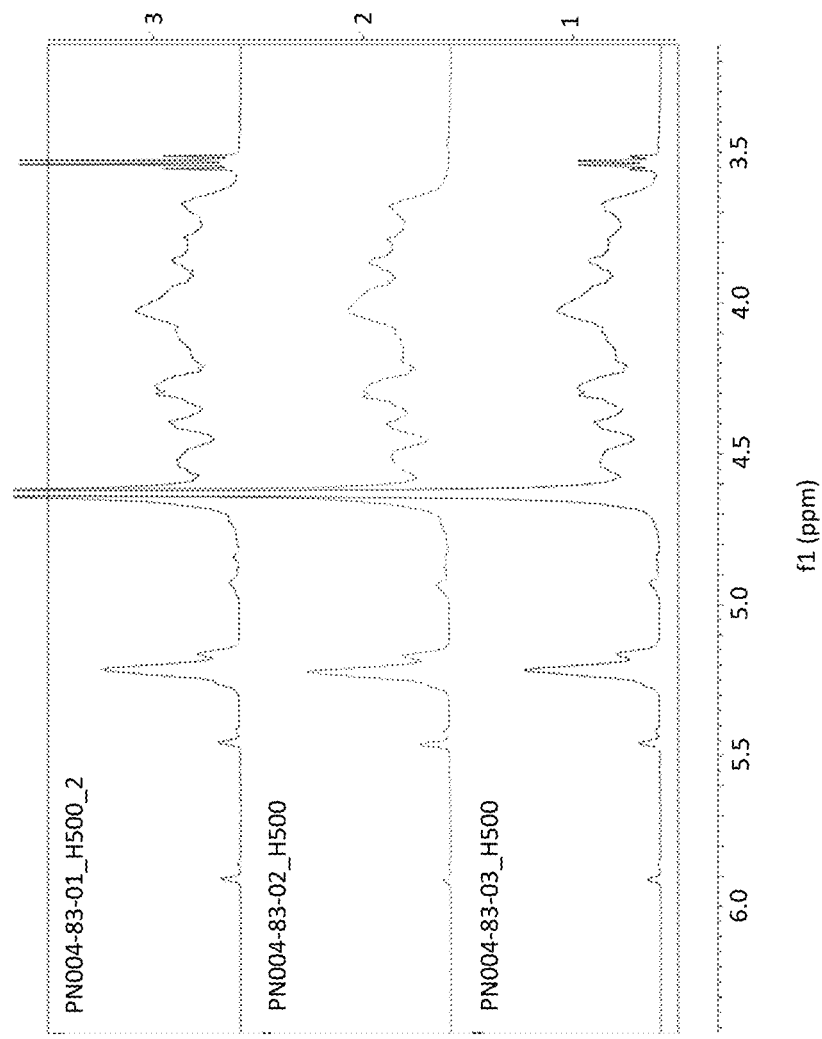
FIG. 6 illustrates a comparison of the dextran sulfate region of 1D $^1$H NMR spectra for dextran sulfate molecules according to the embodiments (top—batch no. 1, middle—batch no. 2, bottom—batch no. 3).

FIG. 6 illustrates a comparison of the dextran sulfate region in 1D 1H NMR spectra of dextran sulfate from batch nos. 1-3 at 25° C.

All TdB samples except the low-sulfated dextran sulfate are modified in the C1-end. The $^{13}$C NMR chemical shifts of C1 are around 74-80 ppm. This indicates that the modification must involve a substitution of the hydroxyl group and that the replacing group is not bound via oxygen. Thus, this C1-modification is not a sulfate or phosphate, and neither can it be a chlorine deemed from the chemical shifts.

TABLE 3

C1 end group characteristics

| Dextran sulfate sample | End group C1 α-configuration | End group C1 β-configuration | Modified end group C1 |
|---|---|---|---|
| Dextran sulfate 3 | — | — | >98% |
| Dextran sulfate 5 LS | 26% | 74% | Not observed |
| Dextran sulfate 5 HS batch no. 20281 | — | — | >98% |
| Dextran sulfate 5 HS batch no. 20300 | — | — | >98% |
| Dextran sulfate batch no. 1 | 46% | 54% | Not observed |
| Dextran sulfate batch no. 2 | 49% | 51% | Not observed |
| Dextran sulfate batch no. 3 | 51% | 49% | Not observed |

Branching

Data do not exclude that the dextran branching is present in the dextran sulfate samples. However, if any such branching is present it is at very low levels, <1-2%.

Degree of Sulfation and Other Chemical Modifications of Dextran Sulfate

Sulfation has been determined using primarily 2D $^1$H-$^{13}$C HSQC data complemented with 1D $^1$H NMR data. With respect to the total degree of sulfation of C2, C3 and C4, an estimate can be obtained from integration of 2D peaks in the $^1$H-$^{13}$C HSQC spectrum. Estimates of average individual C2 and C3 sulfate levels are estimated from combined 1D and 2D data using C1 peaks as reporters on these three neighbors. The sulfation of C4 could not be determined but using the data of overall C2-C4 sulfation, the average degree of C4 sulfation must be considerably lower, definitely <70%.

Data of the dextran sulfate samples (except of dextran sulfate 3) are fully consistent with an average molecular size of ~5 glucose units per dextran sulfate molecule.

TABLE 4

Degree of sulfation of dextran sulfate

| Dextran sulfate sample | Sulfation of C2-C4[γ] | Individual sulfation | | | Sulfation end group α-C1 | Sulfation end group β-C1 | Sulfation of end group C6 |
|---|---|---|---|---|---|---|---|
| | | C2 | C3 | C4 | | | |
| Dextran sulfate 3 | 68% (2.0) | 89% | ND | ND | ND* | ND* | 83% |
| Dextran sulfate 5 LS | 35% (1.1) | 42% | 26% | ND | 13% | 74% | 73% |
| Dextran sulfate 5 HS batch no. 20281 | 65% (2.0) | 93% | ~50% | ND | ND* | ND* | 82% |
| Dextran sulfate 5 HS batch no. 20300 | 76% (2.3) | >95%[†] | ~50% | ND | ND* | ND* | ND |
| Dextran sulfate batch no. 1 | 80% (2.4) | >95% | ~86% | ND | 41% | >95% | 96% |
| Dextran sulfate batch no. 2 | 76% (2.3) | >95% | ~85% | ND | 16% | 93% | 89% |
| Dextran sulfate batch no. 3 | 79% (2.36) | >95% | ~86% | ND | 30% | 83% | 91% |

*Not determined due to modified C1 end.
[†]Only estimated value as exact integration was prevented due to spectral overlap
[γ]Given in percentage and total number of sulfates per C2-C4 unit Besides the investigation of C2-C4 sulfation, characterization of the degree of sulfation of the end groups are also outlined in Table 4 above. Notably, sulfation is considerably higher if the end group β-C1 is present, consistent with less steric hindrance with sulfate in an equatorial position.

Please note that the α- and β-configurations are in equilibrium via the open aldehyde state which, however, is not readily observed but always there at very low levels.

Molecular Weight and Size

All the Certificates of Analysis for the various batches of dextran sulfate investigated report $M_w$ as the molecular size measure. In addition, light scattering data has been determined, see Annex 1, on the dextran sulfate batch nos. 1-3 reporting $M_w$ and $M_n$. The current NMR data provides $M_n$ as output based primarily on end group analysis, i.e. ratio between the peak areas of end groups versus those of middle-groups (NMR peak areas). The average number of glucose units is determined on the dextran starting material and confirmed fully consistent with the NMR data on the corresponding dextran sulfate batch.

TABLE 5 molecular size characteristics in Da of dextran sulfate samples

| Dextran sulfate sample | Average no. of glucose units | Average sulfate no. per glucose unit | $M_n$ (without Na$^+$) | $M_n$ (with Na$^+$) |
|---|---|---|---|---|
| Dextran sulfate 3 | 3.5 | 2.3 | 1223 | 1406 |
| Dextran sulfate 5 LS | 5.1 | 1.3 | 1378 | 1531 |
| Dextran sulfate 5 HS batch no. 20281 | 5.1 | 2.1 | 1706 | 1954 |
| Dextran sulfate 5 HS batch no. 20300 | 5.1 | 2.4 | 1827 | 2109 |
| Dextran sulfate batch no. 1 | 5.1 | 2.7 | 1957 | 2276 |
| Dextran sulfate batch no. 2 | 5.1 | 2.6 | 1891 | 2192 |
| Dextran sulfate batch no. 3 | 5.1 | 2.7 | 1929 | 2241 |

TABLE 6

Comparison of molecular weight data in Da from different techniques

| Dextran sulfate sample | $M_w$ (certificate of analysis) | $M_w$ (light scattering) | $M_n$ (light scattering) | $M_n$ (NMR) |
|---|---|---|---|---|
| Dextran sulfate 3 | 3300 | | | 1406 |
| Dextran sulfate 5 LS | 3200 | | | 1531 |
| Dextran sulfate 5 HS batch no. 20281 | 4016 | | | 1954 |
| Dextran sulfate 5 HS batch no. 20300 | 4645 | | | 2109 |
| Dextran sulfate batch no. 1 | 5699 | 2757 | 2487 | 2276 |
| Dextran sulfate batch no. 2 | 5897 | 3999 | 3192 | 2192 |
| Dextran sulfate batch no. 3 | 7118 | 9713 | 6757 | 2241 |

$M_w$ (certificate of analysis) has been obtained using SEC

This big discrepancy between the molecular weight parameter as determined by NMR and the other molecular weight parameters listed in Table 6 may be explained by that molecular weight of dextran sulfate are normally determined using more indirect methods as gel exclusion/penetration chromatography, light scattering or viscosity. All these methods rather report on the molecular size. This means that if the dextran sulfate molecules form various aggregates or complexes, a higher apparent molecular weight is determined.

These indirect methods rather report on molecular volume and shape, which may differ significantly not only from batch to batch but also from sample to sample within the same batch depending on, for instance, how the dextran sulfate material has been stored, how it is prepared prior to the measurement, etc.

In-Depth Structural Characterization of Dextran Sulfate

Based on a thorough analysis of a set of 1D and 2D NMR data acquired on dextran sulfate batch no. 3, a serious attempt was performed to understand the sulfation pattern at an atomic resolution of this dextran sulfate sample further. Given the close similarity of the 1D $^1$H and 2D $^{13}$C-1H HSQC spectra with dextran sulfate batch nos. 1 and 2, the findings presented in this section are assumed to be valid for dextran sulfate batches of the embodiments in general.

Overall Degree of Sulfation and Sample Composition

Figure 7:
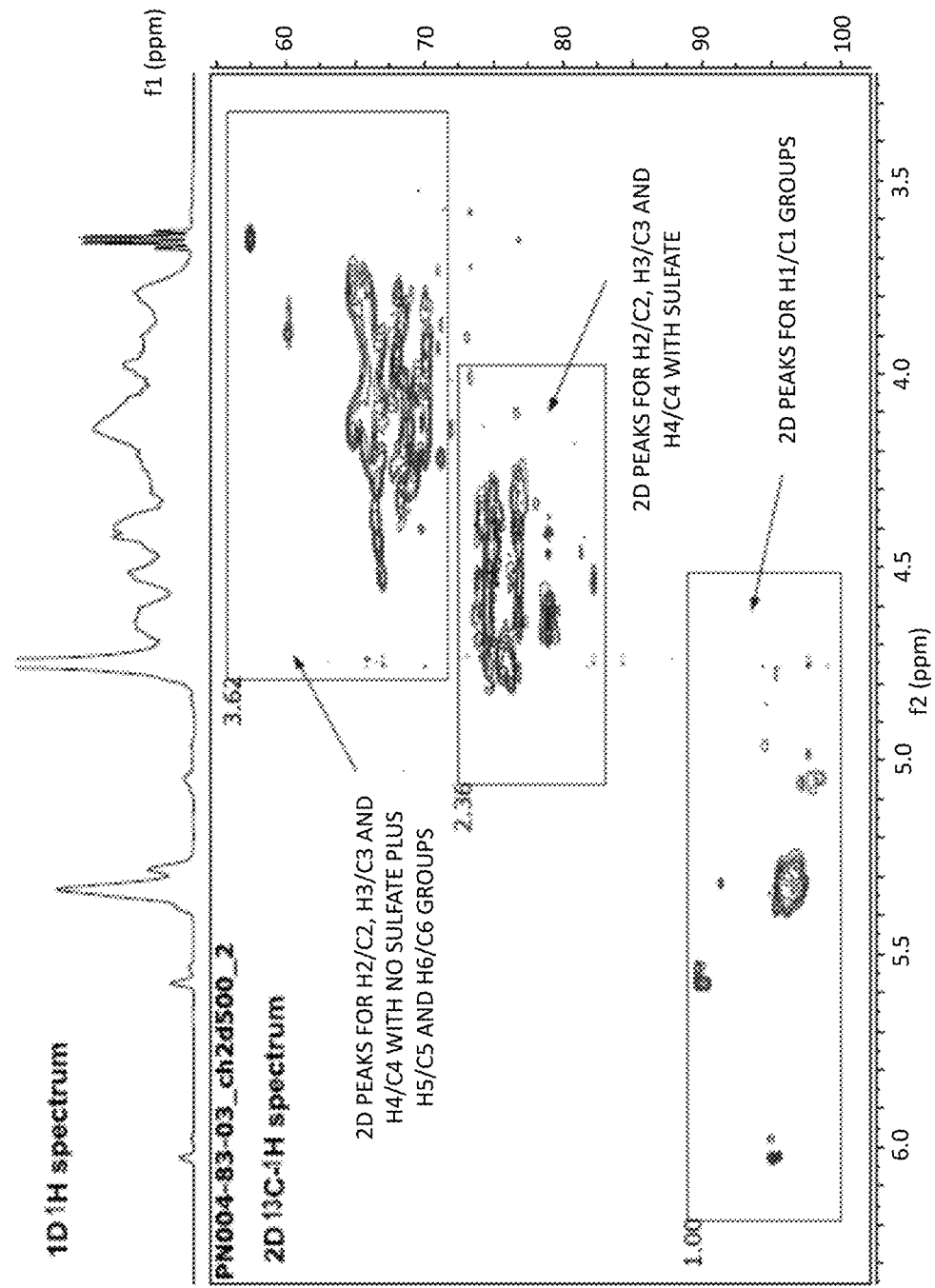
FIG. 7 illustrates 2D $^{13}$C-1H HSQC spectrum of a dextran sulfate of the embodiments (batch no. 3) at 25° C.

Starting from an overview perspective, the $^{13}$C-$^1$H HSQC spectrum permits to determine a relatively accurate estimate of the degree of sulfation, see FIG. 7. Dextran sulfate batch no. 3 has in average 2.4±0.1 sulfate groups per glucose unit at the C2, C3 and C4 positions. Each peak in FIG. 7 corresponds to C—H bond with different chemical environment. Peak areas correspond roughly to the population of each C—H bond. Three distinct areas are observed enabling quantification of the overall degree of dextran sulfation. At the top the corresponding region of the 1D $^1$H spectrum is aligned.

Using an average value of 2.66 sulfates per glucose units and 5.1 glucose units, the calculated weight % of sulfur is about 19% assuming that the sample consists of 100% dextran sulfate.

Investigation of Sulfation at C2, C3 and C4

Due to the highly overlapped regions, sulfation patterns are studied almost exclusively using the $^1$H/$^{13}$C chemical shifts and corresponding peak areas of the H1/C1 groups located in different kinds of glucose units. Based on the 1H/$^{13}$C chemical shift assignments of dextran, literature data and not least on the acquired 2D NMR data, H1/C1 signals were tentatively assigned to specific C1 groups with various chemical environment and degree of sulfation. This assignment is depicted in FIGS. 3 and 4.

Based on the assignments and measurement of 1D $^1$H peaks and associated peak integrals, it appears that the population of the configuration of the anomeric C1-group of C1-terminal glucose has shifted to a more equal, 0.49:0.51 ratio, for α:β configuration assuming that average length of the dextran itself has not changed upon the chemical sulfation procedure. The free α-C1 group is sulfated to ~30% while the degree of sulfation is β-C1 is estimated to be significantly higher and around 83%.

With respect to determining the degree of sulfation of C2, C3 and C4, the analysis is easiest for C2 that is definitely highly sulfated >95%, and assuming that the ratio is correctly estimated for the α:β configuration of C1-terminal glucose the sulfation degree is calculated to ~99%. C3 is sulfated to 82% for glucose units C1 involved in α(1→6) glycosidic linkages, i.e. middle and C6-terminal rings, as well as C1-terminal glucose units with free C1. For C1-terminal glucose units with sulfated C1, the sulfation of C3 appears higher, ~86%. Calculation of number of sulfates per C4 is more difficult but using the overall ratio of 2.4 sulfates per glucose ring and 99% sulfation for C2, 82% sulfation for C3, the degree of sulfation is estimated to be ~60%.

NMR Characterization of Dextran and Dextran Sulfate from Meito

Using the previously established 1D $^1$H and 2D $^{13}$C-$^1$H HSQC NMR methodology for structural characterization of dextran and dextran sulfate, dextran and dextran sulfate samples obtained from Meito Sangyo Co., Ltd. where investigated.

NMR Samples

| | |
|---|---|
| PN004-99-04 | The NMR sample was prepared by dissolving 43.4 mg of dextran from Meito Sangyo Co., Ltd. (batch. no TL-2385) in 520 μl D$_2$O. |
| PN004-99-05 | The NMR sample was prepared by dissolving 58.7 mg of dextran sulfate Sulfur 18 from Meito Sangyo Co., Ltd. (batch no. N-3188) in 520 μl D$_2$O. |

NMR Results

The average number of glucose units in the dextran was determined to be 11.7 with a $M_n$ of 1920 Da. The $M_n$ of dextran sulfate Sulfur 18 was determined to be within 4120 and 4200 Da excluding any sodium counter ion and within 4710 and 4790 Da with the sodium counter ion. The degree of C1 end group in α-configuration was 59% and the degree of branching was estimated to be 4.8%.

The degree of sulfation of positions C2-C4 was determined to be 76% (2.29 sulfate groups per glucose unit). The degree of sulfation of C2 position was estimated to be 93%. The degree of C1 end group in α-configuration was 71% and the degree of sulfation of α-C1 end groups was 83%. The degree of sulfation of C1 end group in β-configuration was >90%. No chemical modifications of C1 end groups besides sulfation were detected.

Comparisons of Biological Effects of Different Dextran Sulfate Molecules

The present studies compare various biological effects of the different dextran sulfate molecules showing that dextran sulfate of the embodiments have superior biological effects while not being toxic.

Comparison on Mobilization of Hematopoietic Cells by Molecular Weight Dextran Sulfate of Different Average Molecular Weights Animals Female DBA/201a mice (Harlan, Holland) were kept at the animal facility at Uppsala University housed under standard conditions and were provided with food and water ad libitum. Animals weighing 17-22 g were used.

Experimental Design

DBA/2-females were grouped into four groups: 1) vehicle (aq. NaCl) (n=8), 2) 50 mg/kg dextran sulfate 3, DS3, (n=5), 3) 50 mg/kg dextran sulfate batch no. 3 (n=5) and 4) 50 mg/kg dextran sulfate batch no. 3, PNB, (n=5). Group 4) was sedated with sodium pentobarbital (PNB) instead of isoflurane, to evaluate if a change in anesthesia protocol affects mobilization.

Administration of Substance

Dextran sulfate of the embodiments (batch no. 3) and dextran sulfate 3 (TdB Consultancy, batch no. 20341, DS3) were dissolved in 0.9% NaCl (Fresenius Kabi), to 20 mg/mL and filtered through 20 μm filter to obtain a sterile solution. The animals received 2.5 mL/kg (app. 50 μL) intravenously through the tail vein.

Hematological Analysis

Figure 8:
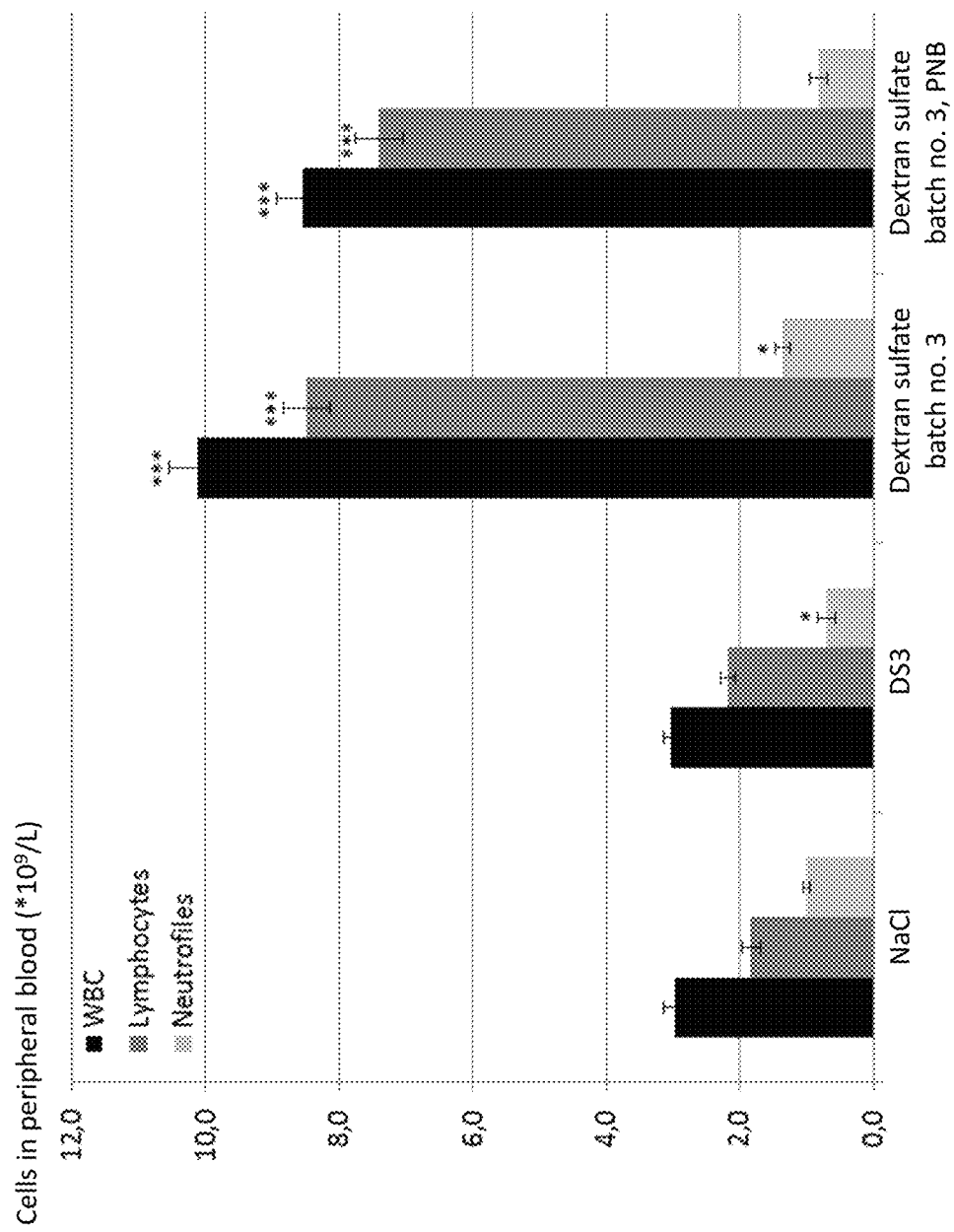
FIG. 8 illustrates the effects of dextran sulfate on white blood cells in peripheral blood. The animals were treated with a single i.v. injection of dextran sulfate of different average molecular weights in doses of 50 mg/kg. Buffered saline (NaCl) was used as vehicle control. Some animals were sedated using penta-sodium barbital (PNB) instead of isoflurane to compare the effect of different methods of anesthesia. Error bars show standard error of mean (SEM). Student t-test was used to evaluate statistically significant differences compared to control group (*$p<0.05$, $p<0.01$, *$p<0.001$).

The results are shown in FIG. 8 and Table 7. Dextran sulfate 3 did not show any significant alteration in overall WBC or lymphocytes whereas a slight decrease in neutrophils was reported.

TABLE 7 hematological variables in peripheral blood after administration of dextran sulfate substances

|  | Unit | Vehicle | DS3 | DS batch no. 3 | DS batch no. 3 PNB |
|---|---|---|---|---|---|
| Platelets | $10^9$/L | 943 ± 40 | 925 ± 30 | 950 ± 31 | 980 ± 11 |
| Hemoglobin | g/L | 128 ± 2 | 128 ± 4 | 129 ± 3 | 135 ± 2* |
| Erythrocytes | $10^{12}$/L | 10 ± 0.1 | 9.6 ± 0.2 | 9.7 ± 0.2 | 10.1 ± 0.2* |
| Hematocrit (EFV) |  | 0.42 ± 0.005 | 0.42 ± 0.008 | 0.43 ± 0.008 | 0.44 ± 0.01* |
| MCV | fL | 44 ± 0.3 | 44 ± 0 | 44 ± 0.4 | 44 ± 0.3 |
| MCHC | g/L | 308 ± 1 | 302 ± 6 | 305 ± 1 | 304 ± 4 |
| Reticulocytes | $10^9$/L | 3 ± 0.4 | 3 ± 0.4 | 4 ± 0.6 | 4 ± 0.4 |
| Leukocytes (WBC) | $10^9$/L | 3 ± 0.2 | 3.0 ± 0.4 | 10.1 ± 1.0*** | 8.5 ± 0.7*** |
| Neutrophils | $10^9$/L | 1.0 ± 0.1 | 0.7 ± 0.1* | 1.4 ± 0.2* | 0.8 ± 0.2 |
| Eosinophils | $10^9$/L | 0.1 ± 0.02 | 0.1 ± 0 | 0.1 ± 0 | 0.1 ± 0 |
| Basophils | $10^9$/L | 0.1 ± 0 | 0.1 ± 0 | 0.1 ± 0 | 0.1 ± 0 |
| Lymphocytes | $10^9$/L | 2 ± 0.1 | 2.2 ± 0.4 | 8.5 ± 0.9*** | 7.4 ± 0.7*** |
| Monocytes | $10^9$/L | 0.05 ± 0.02 | 0.02 ± 0.02 | 0.1 ± 0 | 0.06 ± 0.02 |
| Time of blood sample after DS | min | 31 ± 0.3 | 32 ± 0.4 | 31 ± 0.2 | 33 ± 1.4 |

Figure 9:
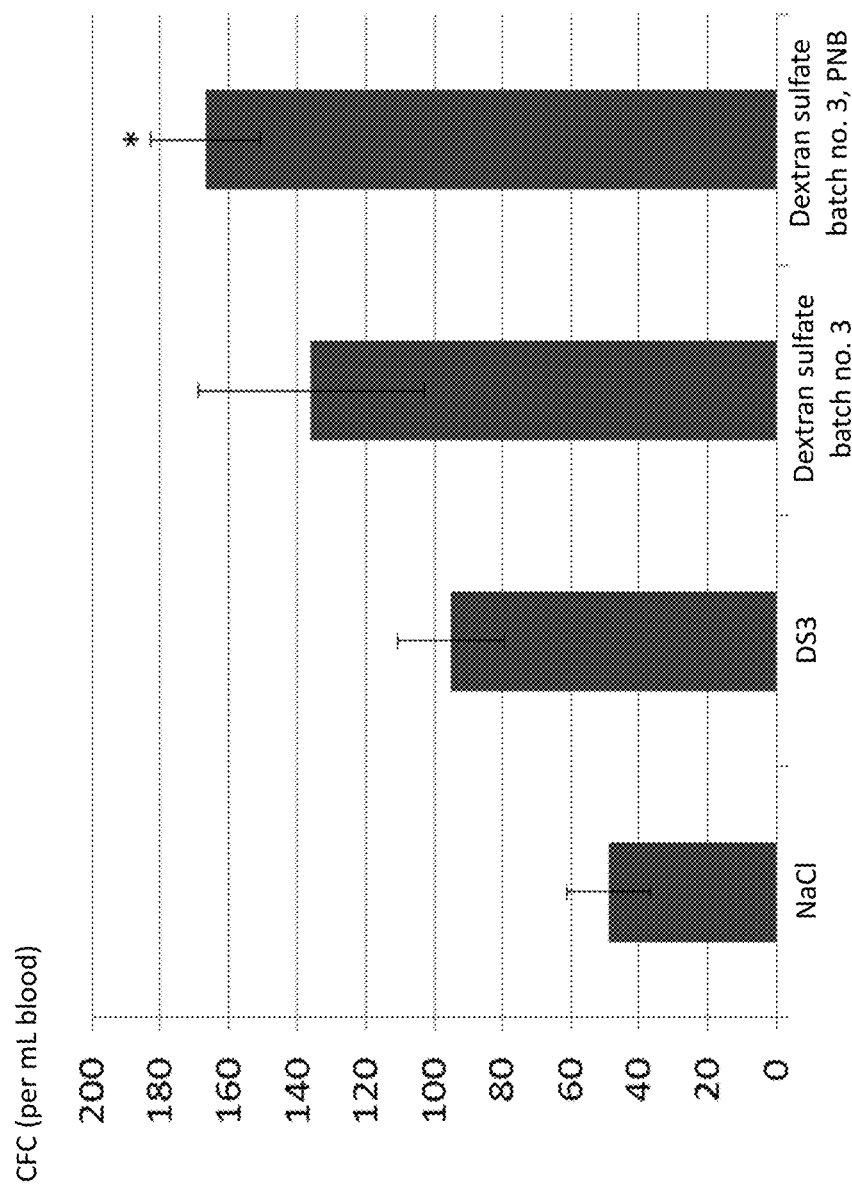
FIG. 9 illustrates the efficacy of dextran sulfate on mobilizing hematopoietic progenitor cells into peripheral blood. Animals were treated with a single i.v. injection of dextran sulfate of different average molecular weight or with vehicle (NaCl). Error bars show SEM. Student t-test was used to evaluate statistically significant differences compared to control group (*$p<0.05$).
Figure 10:
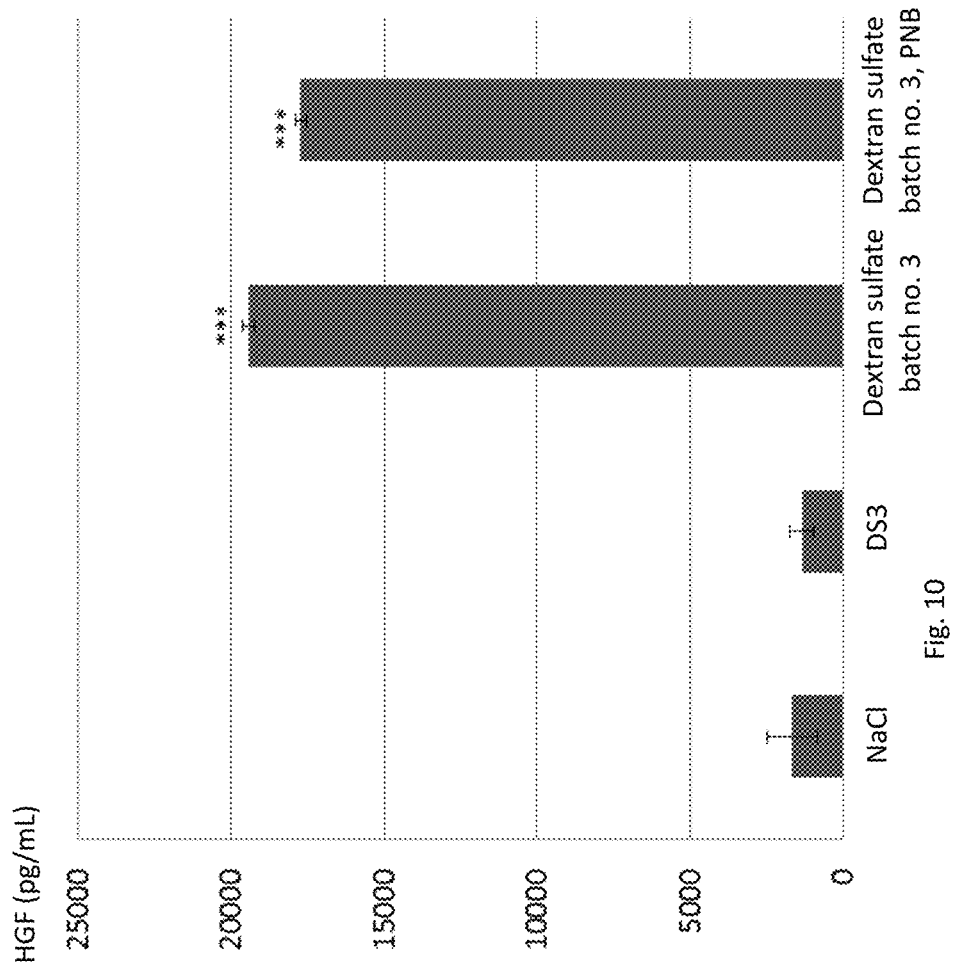
FIG. 10 illustrates the efficacy of dextran sulfate on increasing HGF levels in peripheral blood. Animals were treated with a single i.v. injection of dextran sulfate of different average molecular weight or with vehicle (NaCl). Error bars show SEM. Student t-test was used to evaluate statistically significant differences compared to control group (***$p<0.001$).

MVC = Mean Corpuscular Volume;
MCHC = Mean Corpuscular Hemoglobin Concentration Hematological variables compared to vehicle (NaCl):
*$p < 0.05$,
**$p < 0.01$,
***$p < 0.001$ Dextran sulfate 3 did not induce a significant increase in the number of CFC, as shown in FIG. 9. Dextran sulfate batch no. 3 induced a significant increase in HGF independent of the use of anesthesia, whereas the lower molecular weight substance 3 showed no significant increase in HGF, see FIG. 10. The data presented herein shows that dextran sulfate 3 is a poor mobilizing agent compared to the dextran sulfate of the embodiments. Dextran sulfate 3 did not increase HGF to any degree beyond vehicle.

Comparison on Preventive Treatment by Molecular Weight Dextran Sulfates in $MOG_{1-125}$ Induced Chronic EAE The objective of this study was to compare the preventative treatment effects of a dextran sulfate of the embodiments (batch no. 3) with dextran sulfate 5 HS (TdB Consultancy, batch no. 20300) in $MOG_{1-125}$ induced experimental autoimmune encephalomyelitis (EAE).

Animals

All animal experiments were carried out according to the National Institute of Health (NIH) guidelines for the care and use of laboratory animals, and approved by the Finnish National Animal Experiment Board.

Altogether 90 female Dark Agouti rats, weighing 120-170 g, purchased from Harlan Laboratories, UK were used in experiments. Animals were housed at a standard temperature (22±1° C.) and in a light-controlled environment (lights on from 7 am to 8 μm) with ad libitum access to food (Harlan 2016) and water. Animals were grouped as follows:

Group 1: 15 EAE rats treated s.c. once-a-day, three times a week with vehicle (saline) starting on day 0 after inoculation of MOG EAE and continued according to the dosing schedule until end-point.

Group 2: 15 EAE rats treated s.c. once-a-day, three times a week with dextran sulfate 5 HS (TdB Consultancy, batch no. 20300) (30.0 mg/kg) starting on day 0 after inoculation and continued according to the dosing schedule until end-point.

Group 3: 15 EAE rats treated s.c. once-a-day, three times a week with a dextran sulfate according to the embodiments (batch no. 3) (30.0 mg/kg) starting on day 0 after inoculation and continued according to the dosing schedule until end-point.

Induction and Clinical Scoring of EAE

EAE was induced by administration of 100 μL inoculum intradermally at the base of the tail. The inoculum consisted of 20 μg of recombinant MOG1-125 (NordicBioSite) in PBS (0.01 M) emulsified with incomplete Freund's adjuvant (IFA) (Sigma F5506) (1:1) containing 200 μg of heat-inactivated *Mycobacterium tuberculosis* (strain H 37 RA; Difco, Detroit, Mich.).

Clinical scoring was performed every day for the 36 Study days, starting on day 0 and continued until the end-point day 35. Clinical scoring was performed blinded during the course of the study and according to the Clinical Scoring Principles listed below.

| Score | Manifestations |
|---|---|
| 0 | Normal |
| 0.5 | Partial tail weakness |
| 1.0 | Complete tail paralysis (all of tail dragged along) |
| 2.0 | Partial weakness in one limb (usually hind limb) |
| 2.5 | Complete paralysis in one limb - (no movement preserved in affected limb). |
| 3.0 | Partial weakness in both hind limbs |
| 3.5 | Complete paralysis in both hind-limbs (no movement in hind limbs), or partial weakness in limbs on one side of the body (hemiparesis). |
| 4 | Partial weakness in all four limbs or complete weakness on one side of the body (hemiplegia). |
| 5 | Complete paralysis of all four limbs (tetraplegia), moribund. |

Cumulative disease index (CDI) is indicated as cumulative disease burden, the sum of the Clinical Score values, during the course of the Study. Disease onset (DO) indicates the Study day when the visible symptoms of EAE have been observed for the first time (Clinical Score value ≥0.5).

All the rats in the Study received the dextran sulfates or corresponding vehicle between days 0 and 34 according to the following dosing schedule:

Group 1 received vehicle (saline, 9 mg/ml, Baxter) administered subcutaneously (s.c.) three times a week (Mon-Wed-Fri) between 7-11 a.m. The dosing volume for vehicle was 5.0 ml/kg. Vehicle administration was started on day 0 after induction of MOG EAE and continued until either Study day 32 or Study day 33 depending on the weekday of the inoculation and the dosing schedule.

Group 2 received dextran sulfate 5 HS (TdB Consultancy, batch no. 20300) with the dose of 30.0 mg/kg administered subcutaneously (s.c.) three times a week (Mon-Wed-Fri) between 7-11 a.m. The dosing volume was 5.0 ml/kg. Administration was started on day 0 after induction of MOG EAE and continued until either Study day 32 or Study day 33 depending on the weekday of the inoculation and the dosing schedule.

Group 3 received a dextran sulfate according to the embodiments (batch no. 3) with the dose of 30.0 mg/kg administered subcutaneously (s.c.) three times a week (Mon-Wed-Fri) between 7-11 a.m. The dosing volume was 5.0 ml/kg. Administration was started on day 0 after induction of MOG EAE and continued until either Study day 32 or Study day 33 depending on the weekday of the inoculation and the dosing schedule.

End-Point Tissue and Plasma Collection

At the end-point, on day 35, all rats were deeply anesthetized with pentobarbital (Mebunat®, 60 mg/ml, Orion Pharma). After this, blood samples were collected via cardiac puncture. The total of 800-1000 µl of blood was collected into Li-heparin micro tubes and centrifuged with 2000×G for 10 minutes at +4° C. Two 200 µl aliquots of plasma were collected into two separate plasma-collecting matrix polypropylene tubes, frozen on dry ice and are stored at −80° C. until either used for further analysis.

For histological samples, rats were transcardially perfused for 10 min with cold heparinized (2.5 IU/ml) saline followed by at least 10 min perfusion with cold 4% paraformaldehyde in 0.1 M phosphate buffer. The cerebellum and the rest of brains and spinal cord C and T-segments (1 cm each) were excised and post-fixed by immersion in 4% paraformaldehyde in 0.1 M phosphate buffer at +4° C. for at least 24 h. The samples were then changed to 0.01 M PBS containing 0.001% sodium azide (Sigma) as preservative, stored at +4° C. until used for possible histological analysis.

General Health Status and Humane End-Points

Animals were monitored twice-a-day by laboratory personnel (8 am and 4 µm). In case of the general health status of an animal got significantly worse, the rat was euthanized by an overdose of $CO_2$ and neck dislocation. Euthanized rats or rats found dead were subjected to macroscopic examination as soon as possible after death. When necropsy was not immediate, carcasses were refrigerated at ~4° C. until necropsy was performed at Charles River DRS, Finland. Definitions of acceptable endpoints included: no spontaneous movements and inability to drink or eat in 24-h observation period, massive bleeding, spontaneous inflammation, missing anatomy, swelling or tumors.

Model (EAE) specific end-points justifying the euthanizing of the rat included: clinical score reaching level 4 (partial weakness in all limbs or hemiplegia), righting reflex >30 seconds, and the dropping of body weight for over 25% from the baseline.

Statistical Analysis

All values are presented as mean±standard deviation (SD) or standard error of mean (SEM), and differences are considered to be statistically significant at the P<0.05 level. Statistical analysis was performed by using StatsDirect statistical software. Differences among means were analyzed by using 1-way-ANOVA followed by Dunnet's test (comparison to the vehicle treated group). Non-parametric data was analyzed with Kruskal-Wallis ANOVA (between groups).

Body Weight

The body weight of the rats was monitored daily starting from day 0 and continued until End-point day 35. All rats in groups 2 and 3 gained weight similar to the vehicle group 1 during the course of the Study (p>0.05).

Disease Incidence and Survival

For all the rats in the Study, the mortality by groups was as follows:

Group 1: 40% (6/15);

Group 2: 20% (4/15); and

Group 3: 7% (1/15).

Cumulative Disease Index

The Cumulative Disease Index (CDI) indicates the sum of Clinical Score values during the 36 days; from inoculation day 0 to the end-point day 35. High value of the index represents an advanced disease and low value of the index indicates mild symptoms.

Figure 11:
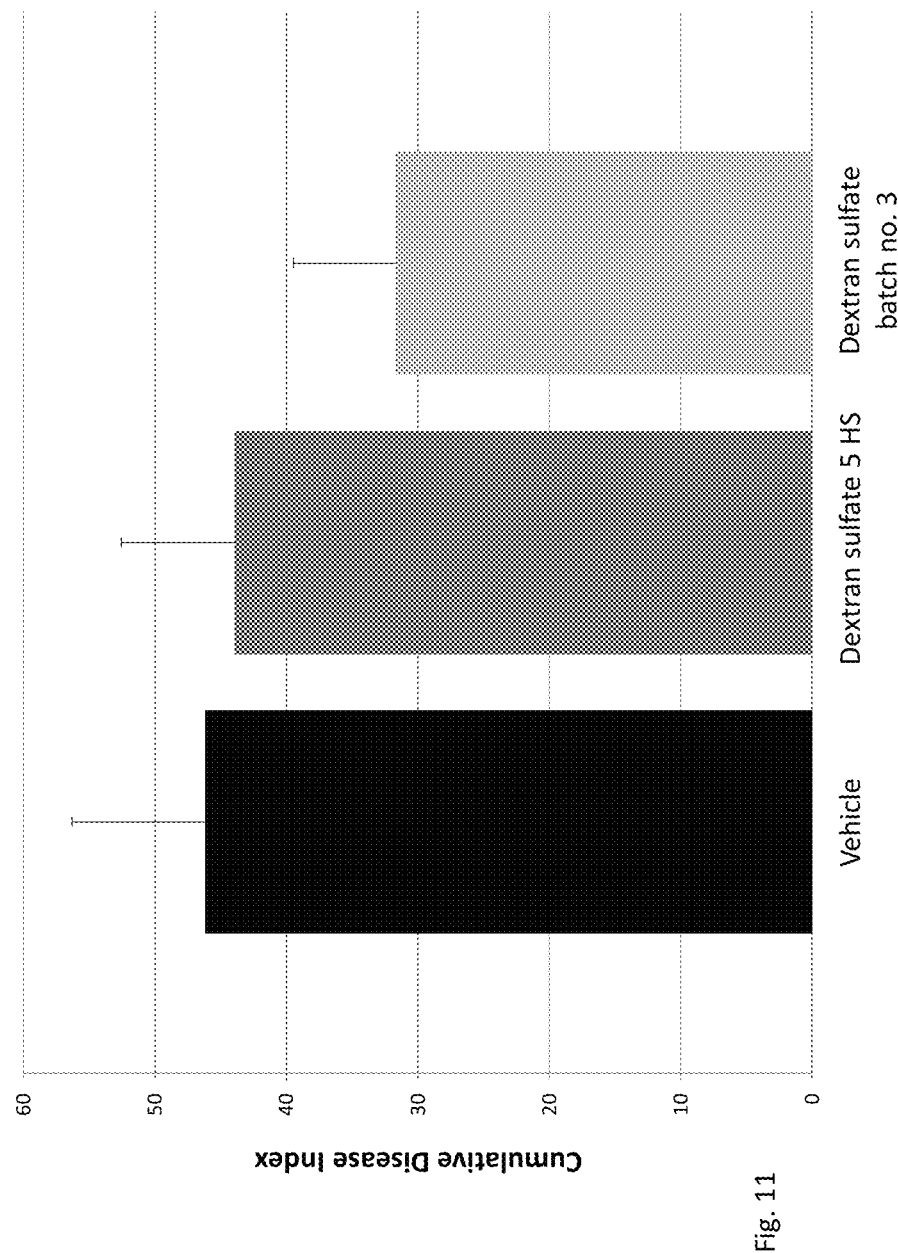
FIG. 11 illustrates the effects of administered dextran sulfate 5 HS (30.0 mg/kg) and a dextran sulfate of the embodiments (batch no. 3, 30 mg/kg) and vehicle on cumulative disease index.

The effects of subcutaneously administered dextran sulfate compounds and the vehicle on Cumulative Disease Index are presented in FIG. 11. There were no significant differences in Cumulative Disease Index between vehicle group animals (group 1) and group 2. However, dextran sulfate treatment in group 3 reduced the mean CDI by 31% compared to vehicle.

Hence, the dextran sulfate according to the embodiments (batch no. 3) had improved biological effects as assessed by CDI as compared to dextran sulfate 5 HS for subjects with EAE.

EAE is an animal model of inflammatory demyelinating diseases of the central nervous system (CNS). It is widely studied as an animal model of the human CNS demyelinating diseases, including multiple sclerosis (MS) and acute disseminated encephalomyelitis (ADEM). Hence, the dextran sulfate of the embodiments seem to have beneficial effects in terms of treating or at least reducing the symptoms of MS and ADEM.

Comparison of Toxicity Between Dextran Sulfate Molecules

Toxicity in Sprague-Dawley rats by single dose dextran sulfate administered by i.v. injection was evaluated during a 2 week observation period. The vehicle used in these experiments was 75 mM CAM in 0.9% NaCl.

In this study, a dextran sulfate of the embodiments (batch no. 3) and dextran sulfate (DS-18) produced by Meito Sangyo Co., Ltd. (batch nos. N-3188 and N-3190) were given to male Sprague Dawley rats by single bolus injection at the dose levels 70 and 140 mg/kg with an observation period of 14 days. The study comprised in total of 7 groups as follows; one control; DS-S18, batch no. N-3188; DS-S18 batch no. N-3190; and dextran sulfate batch no. 3, see Table 8. Five animals were included in each dose group except for dextran sulfate batch no. 3, 70 mg/kg in which 10 animals were included. Pathology was performed on the lungs from all animals in the study and on selected organs in the groups treated with dextran sulfate batch no. 3 (adrenal glands, femur with bone marrow, heart, kidneys, liver, mesenteric lymph nodes, spleen, thymus and the injection site).

TABLE 8

| | experimental design | | | | | | |
|---|---|---|---|---|---|---|---|
| Group | 1 | 2 | 3 | 4 | 5 | 6 | 7 |
| Dose (mg/kg) | 0 | 70 | 140 | 70 | 140 | 70 | 140 |
| Compound (batch no.) | vehicle | DS-S18 (N-3188) | | DS-S18 (N-3190) | | DS batch no. 3 | |
| No. of animals | 5 | 5 | 5 | 5 | 5 | 10 | 5 |

No deaths occurred in the study. On the day of dosing (day 1) animals receiving dextran sulfate showed dyspnea, about 10 min after dosing in all groups with some degree of dose relationship. The highest incidence was observed in animals given 140 mg/kg. The severity observed in most animals was slight except for those receiving 140 mg/kg of DS-S18, batch N-3188 which showed moderate dyspnea in four out of five animals. During the remaining observation period (days 2-15) most animals given 140 mg/kg of DS-S18, both batches, showed dyspnea. One animal given dextran sulfate batch no. 3 showed dyspnea days 6-15.

At histological examination treatment related changes in animals dosed with the test compounds were observed in the lungs and consisted of alveolar histiocytosis and alveolar septal thickening/increased cellularity. An increased incidence and severity of these changes was noted in the majority of animals receiving 140 mg/kg of both batches of the test compound DS-S18. Only one single animal out of ten receiving 70 mg/kg of dextran sulfate batch no. 3 showed minimal changes, and three out of five receiving 140 mg/kg showed minimal to moderate findings. In addition to the lung findings a marginally increased degree of extramedullary haematopoiesis was noted in the spleen at all dose groups, however, considered to be of questionable toxicological significance.

Of the compounds tested in the present study, dextran sulfate batch no. 3 showed less pronounced lung toxicity than DS-18.

NMR Analysis of Dextran Sulfate from Sigma-Aldrich

Structural characteristics of a dextran sulfate sodium salt (DSS) from Sigma-Aldrich (product no. 31404) has been determined using 1D 1H and 2D 13C-1H HSQC NMR spectroscopy. The Certificate of Analysis from Sigma-Aldrich with regard to the dextran sulfate (product no. 31404) indicates a molecular weight ($M_r$) of 5000 Da and an average sulfur content is 17%, which is equivalent to approximately 2.3 sulfate groups per glucosyl residue.

The NMR sample was prepared by dissolving 35.9 mg of dextran sulfate from Sigma-Aldrich (product no. 31404) in 510 μl D2O.

Results
Number of glucose units: 26-50
$M_n$: 8600-16900 Da
Degree of C1 in α-configuration: not determined but >50% (α-configuration>>β-configuration)
Degree of sulfation C2-C4: 74%
Degree of sulfated α-C1 end group: 49%
Degree of sulfated β-C1 end group: not determined The most precise method to determine the number of glucose units in dextran sulfate molecules is to perform simultaneous analysis of the corresponding dextran used as starting material for the dextran sulfate production. Without NMR data on the corresponding dextran, the spectral over-

TABLE 9

Figure 13:
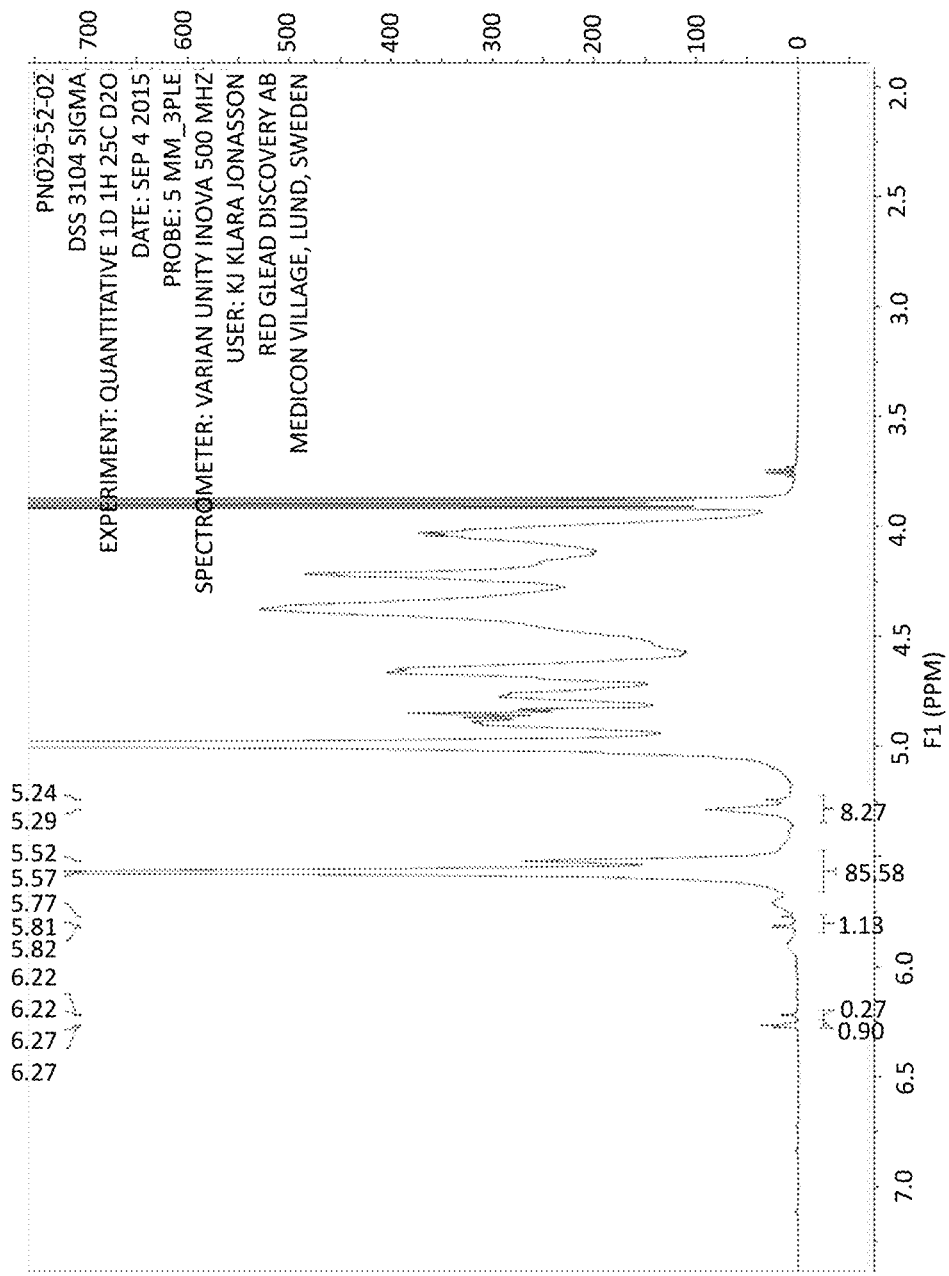
FIG. 13 illustrates 1D $^1$H NMR spectrum of a dextran sulfate according to prior art.

| incidence and severity of microscopic changes in the lung of treated animals | | | | | | | |
|---|---|---|---|---|---|---|---|
| Group | 1 | 2 | 3 | 4 | 5 | 6 | 7 |
| Dose (mg/kg) | 0 | 70 | 140 | 70 | 140 | 70 | 140 |
| Compound (batch no.) | vehicle | DS-S18 (N-3188) | | DS-S18 (N-3190) | | DS batch no. 3 | |
| No. of animals | 5 | 5 | 5 | 5 | 5 | 10 | 5 |
| Lung alveolar histiocytosis | | | | | | | |
| minimal focal | 0 | 0 | 1 | 2 | 0 | 1 | 2 |
| minimal multifocal | 0 | 0 | 0 | 1 | 0 | 0 | 0 |
| slight | 0 | 0 | 3 | 0 | 3 | 0 | 1 |
| Total incidence | 0 | 0 | 4 | 3 | 3 | 1 | 3 |
| Alveolar septa thickening/increased cellularity | | | | | | | |
| minimal focal | 0 | 0 | 0 | 1 | 0 | 1 | 1 |
| minimal multifocal | 0 | 0 | 0 | 0 | 0 | 0 | 0 |
| slight | 0 | 0 | 0 | 0 | 0 | 0 | 0 |
| moderate | 0 | 0 | 3 | 0 | 3 | 0 | 1 |
| Total incidence | 0 | 0 | 3 | 1 | 3 | 1 | 2 |
| Alveolar haemorrhages | | | | | | | |
| minimal focal | 0 | 0 | 0 | 1 | 0 | 2 | 2 |
| minimal multifocal | 0 | 0 | 0 | 0 | 1 | 0 | 0 |
| slight | 0 | 0 | 1 | 0 | 0 | 0 | 0 |
| Total incidence | 0 | 0 | 1 | 1 | 1 | 2 | 2 | lap in the region of 4.8-5.2 ppm in the 2D 13C-1H HSQC spectrum, see FIG. 14, prevents quantification of the fraction end-C1 in R-anomer configuration as well as the degree of sulfated β-C1 end groups. FIG. 13 illustrates the 1D $^1$H NMR spectrum for dextran sulfate from Sigma Aldrich (product no. 31404).

Thus, the calculated number of glucose units in the sample dextran sulfate (product no. 31404) is reported as an interval, with the degree of terminal C1 in the α-configuration ranging from 50% to 100%. The 2D $^{13}$C-$^1$H HSQC spectrum data displays no signals in the expected region of the β-C1 end group suggesting that the number of glucose units lies in the upper part of the reported interval.

Discussion

The NMR results indicate that the molecular weight of dextran sulfate with molecular weight $M_r$ 5000 Da from Sigma-Aldrich (product no. 31404) actually has a number average molecular weight $M_n$ as measured by NMR-spectroscopy within an interval of 8600 Da and 16900 Da.

Functional Test of Dextran Sulfate from Different Manufactures

The aim of this study was to investigate and compare the functional effect of dextran sulfate from different manufactures on activated partial thromboplastin time (APTT) in an ex vivo human assay.

APTT is a medical test that characterizes blood coagulation. Apart from detecting abnormalities in blood clotting, it is also a performance indicator of the efficacy of both the contact activation pathway and the common coagulation pathways.

Method and Equipment

APTT was measured in human plasma using the Start® 4 from Diagnostica Stago according to the manufacturer's instruction. Dextran sulfate was dissolved to 1 mg/ml in 75 mM citrate buffer with an initial pH of 5.9 and then added to the human plasma to a final dextran sulfate concentration of 10 μg/ml.

Four different dextran sulfate batches from Meito Sangyo Co., Ltd., Japan (N-3178, N-3179, N-3180, N-3181), one dextran sulfate batch from Sigma-Aldrich, U.S. (average molecular weight 5000 Da, product no. 31404) and two dextran sulfate batches (batch no. 1 and batch no. 2) according to the embodiments were analyzed. From each batch four separately weighted samples were processed and on each of these samples the APTT was measured in duplicates. All sample handling was performed in parallel and on the same day. In the next day all APTT measurements was performed on all samples to obtain comparable results.

The use of plasma instead of whole blood in the APTT analysis makes the analysis more robust and the results vary less.

Results

The results from the APTT analysis is presented in Table 10 below. Baseline for APTT was plasma measured as a negative control.

TABLE 10

APTT in plasma after dextran sulfate treatment

| Dextran sulfate | APTT (s) | Mean | SEM |
| --- | --- | --- | --- |
| Negative control | 27.5 | | |
| Meito N-3178 | 56.3 | 59.5 | 1.1 |
| Meito N-3179 | 60.2 | | |
| Meito N-3180 | 62.2 | | |
| Meito N-3181 | 59.1 | | |
| Sigma Aldrich 31404 | 78.6 | | |

TABLE 10-continued

APTT in plasma after dextran sulfate treatment

| Dextran sulfate | APTT (s) | Mean | SEM |
| --- | --- | --- | --- |
| Batch no. 1 | 49.1 | 51.8 | 2.7 |
| Batch no. 2 | 54.5 | | |

There was a significant difference in APTT as measured for dextran sulfate according to the embodiments and dextran sulfate from other manufactures. In particular, dextran sulfate (5000 Da, product no. 31404) from Sigma-Aldrich resulted in a significantly higher APTT as compared to dextran sulfate according to the embodiments.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

ANNEX 1

The light scattering experiments were conducted on a Size-Exclusion Chromatography MultiAngle Laser Light Scattering (SEC-MALLS) system consisting of an Agilent 1260 Infinity series HPLC system and a connected MiniDAWN TREOS light scattering detector (Wyatt Technologies). The following analysis parameters were used in the light scattering experiments:

Flow=1.00 mL/min.
Column/dRI detector temperature=40° C.
Collection Interval=0.5 s.
Injection volume=10 μL
Dn/dc=0.1470 mL/g
MALLS wavelength=656 nm
Calibration constant (MALLS)=4.7303×10^−5 1/(V cm)

The dextran sulfate sample was dissolved in 2 mL 0.1 M sodium nitrate ($NaNO_3$) with 400 ppm sodium azide ($NaN_3$) as mobile phase (eluent).

The invention claimed is:

1. A method of treating and/or inhibiting instant blood-mediated inflammatory reaction (IBMIR), the method comprising administering, to a subject, a dextran sulfate characterized by:
    a number average molecular weight ($M_n$) as measured by nuclear magnetic resonance (NMR) spectroscopy within an interval of 1850 and 3500 Da;
    an average sulfate number per glucose unit within an interval of 2.5 and 3.0; and
    an average sulfation of C2 position in the glucose units of said dextran sulfate of at least 90%,
    or a salt of said dextran sulfate.

2. The method according to claim 1, wherein said $M_n$ as measured by NMR spectroscopy is within an interval of 1850 and 2500 Da.

3. The method according to claim 2, wherein said $M_n$ as measured by NMR spectroscopy is within an interval of 1850 and 2300 Da.

4. The method according to claim 1, wherein said average sulfate number per glucose unit is within an interval of 2.5 and 2.8.

5. The method according to claim 4, wherein said average sulfate number per glucose unit is within an interval of 2.6 and 2.7.

6. The method according to claim 1, wherein said average sulfation of said C2 position is at least 95%.

7. The method according to claim 1, wherein an average sulfate number at C2, C3 and C4 positions in said glucose units is within an interval of 2.2 and 2.6.

8. The method according to claim 7, wherein said average sulfate number at said C2, C3 and C4 positions is within an interval of 2.3 and 2.5.

9. The method according to claim 1, wherein said dextran sulfate has an average number of glucose units within an interval of 4.0 and 6.0.

10. The method according to claim 9, wherein said average number of glucose units is within an interval of 4.5 and 5.5.

11. The method according to claim 10, wherein said average number of glucose units is within an interval of 5.0 and 5.2.

12. The method according to claim 1, wherein said dextran sulfate has an average branching of glucose units that is less than 3.0%.

13. The method according to claim 12, wherein said average branching is less than 1.5%.

14. The method according to claim 1, wherein said salt of dextran sulfate is a sodium salt and said sodium salt of dextran sulfate including $Na^+$ counter ions has a $M_n$ as measured by NMR spectroscopy within an interval of 2000 and 2500 Da.

15. The method according to claim 14, wherein said sodium salt of dextran sulfate including said $Na^+$ counter ion has a $M_n$ as measured by NMR spectroscopy within an interval of 2100 and 2300 Da.

16. The method according to claim 1, wherein an end group C1 position is sulfated or is bound to —OH.

17. The method according to claim 1, wherein administering said dextran sulfate comprises administering said dextran sulfate by intravenous injection or subcutaneous injection to said subject.

18. The method according to claim 1, wherein administering said dextran sulfate comprises administering, to said subject, an aqueous injection solution comprising said dextran sulfate and a solvent or excipient.

19. The method according to claim 1, wherein administering said dextran sulfate comprises administering from 0.05 to 50 mg dextran sulfate per kg of body weight of the subject.

20. The method according to claim 19, wherein administering said dextran sulfate comprises administering from 0.1 to 40 mg dextran sulfate per kg of body weight of the subject.

21. The method according to claim 20, wherein administering said dextran sulfate comprises administering from 0.1 to 30 mg dextran sulfate per kg of body weight of the subject.

22. The method according to claim 20, wherein administering said dextran sulfate comprises administering from 0.1 to 15 mg dextran sulfate per kg of body weight of the subject.

* * * * *

UNITED STATES PATENT AND TRADEMARK OFFICE
CERTIFICATE OF CORRECTION

PATENT NO. : 10,730,960 B2
APPLICATION NO. : 16/520930
DATED : August 4, 2020
INVENTOR(S) : Lars Bruce et al.

Page 1 of 1

It is certified that error appears in the above-identified patent and that said Letters Patent is hereby corrected as shown below:

On the Title Page

Item (30), change "1451349" to --1451349-3--.

Signed and Sealed this
Twentieth Day of October, 2020

Andrei Iancu
*Director of the United States Patent and Trademark Office*